US010039276B2

(12) United States Patent
Hassanein et al.

(10) Patent No.: US 10,039,276 B2
(45) Date of Patent: Aug. 7, 2018

(54) SYSTEMS, METHODS, COMPOSITIONS AND SOLUTIONS FOR PERFUSING AN ORGAN

(71) Applicant: TransMedics, Inc, Andover, MA (US)

(72) Inventors: Waleed H. Hassanein, North Andover, MA (US); Tamer I. Khayal, North Andover, MA (US); Paul Lezberg, Westford, MA (US)

(73) Assignee: TRANSMEDICS, INC., Andover, MA (US)

( * ) Notice: Subject to any disclaimer, the term of this patent is extended or adjusted under 35 U.S.C. 154(b) by 0 days.

(21) Appl. No.: 14/734,769

(22) Filed: Jun. 9, 2015

(65) Prior Publication Data

US 2015/0342176 A1    Dec. 3, 2015

Related U.S. Application Data

(62) Division of application No. 11/246,919, filed on Oct. 7, 2005, now Pat. No. 9,078,428.

(60) Provisional application No. 60/725,168, filed on Oct. 6, 2005, provisional application No. 60/694,971, filed on Jun. 28, 2005.

(51) Int. Cl.
*A01N 1/02* (2006.01)

(52) U.S. Cl.
CPC ............. *A01N 1/02* (2013.01); *A01N 1/0226* (2013.01); *A01N 1/0247* (2013.01)

(58) Field of Classification Search
CPC ....... A01N 1/02; A01N 1/0226; A01N 1/0247
See application file for complete search history.

(56) References Cited

U.S. PATENT DOCUMENTS

| | | | |
|---|---|---|---|
| 3,253,595 A | 5/1966 | Keller, Jr. et al. | |
| 3,388,803 A | 6/1968 | Scott | |
| 3,406,531 A | 10/1968 | Koski et al. | |
| 3,468,136 A | 9/1969 | Koski et al. | |
| 3,537,956 A | 11/1970 | Falcone | |
| 3,545,221 A | 12/1970 | Koski et al. | |
| 3,545,605 A | 12/1970 | Robins | |
| 3,587,567 A | 6/1971 | Schiff | |
| 3,607,646 A | 9/1971 | de Roissart | |
| 3,632,473 A | 1/1972 | Belzer et al. | |
| 3,639,084 A | 2/1972 | Goldhaber | |
| 3,654,085 A | 4/1972 | Fritz et al. | |
| 3,660,241 A | 5/1972 | Michielsen | |
| 3,738,914 A | 6/1973 | Thorne et al. | |
| 3,772,153 A | 11/1973 | De Roissart | |
| 3,777,507 A | 12/1973 | Burton et al. | |
| 3,843,455 A | 10/1974 | Bier et al. | |
| 3,851,646 A | 12/1974 | Sarns | |
| 3,881,990 A | 5/1975 | Burton et al. | |
| 3,995,444 A | 12/1976 | Clark et al. | |
| 4,186,565 A | 2/1980 | Toledo-Pereyra | |
| 4,231,354 A | 11/1980 | Kurtz et al. | |
| 4,415,556 A | 11/1983 | Bretschneider | |
| 4,598,697 A | 7/1986 | Numazawa et al. | |
| 4,605,644 A | 8/1986 | Foker | |
| 4,666,425 A | 5/1987 | Fleming | |
| 4,719,201 A | 1/1988 | Foker | |
| 4,723,939 A | 2/1988 | Anaise | |
| 4,745,759 A | 5/1988 | Bauer et al. | |
| 4,759,371 A | 7/1988 | Franetzki | |
| 4,801,299 A * | 1/1989 | Brendel ............. A61L 27/3633 128/DIG. 8 |
| 4,847,470 A | 7/1989 | Bakke | |
| 4,920,044 A | 4/1990 | Bretan, Jr. | |
| 5,051,352 A | 9/1991 | Martindale et al. | |
| 5,066,578 A | 11/1991 | Wikman-Coffelt | |
| 5,141,847 A | 8/1992 | Sugimachi et al. | |
| 5,145,771 A | 9/1992 | Lemasters et al. | |
| 5,157,930 A | 10/1992 | McGhee et al. | |
| 5,200,398 A | 4/1993 | Strasberg et al. | |
| 5,217,860 A | 6/1993 | Fahy et al. | |
| 5,285,657 A | 2/1994 | Bacchi et al. | |
| 5,306,711 A | 4/1994 | Andrews | |
| 5,326,706 A | 7/1994 | Yland et al. | |
| 5,338,662 A | 8/1994 | Sadri | |
| 5,356,593 A | 10/1994 | Heiberger et al. | |
| 5,356,771 A | 10/1994 | O'Dell | |
| 5,358,931 A | 10/1994 | Rubinsky et al. | |
| 5,362,622 A | 11/1994 | O'Dell et al. | |
| 5,370,989 A | 12/1994 | Stern et al. | |
| 5,381,510 A | 1/1995 | Ford et al. | |
| 5,385,821 A | 1/1995 | O'Dell et al. | |
| 5,395,314 A | 3/1995 | Klatz et al. | |
| 5,405,742 A | 4/1995 | Taylor | |

(Continued)

FOREIGN PATENT DOCUMENTS

| | | |
|---|---|---|
| CA | 2881613 A1 | 11/2007 |
| CN | 1232723 A | 10/1999 |
| CN | 1269471 A | 10/2000 |
| DE | 4201259 A1 | 7/1993 |
| DE | 10121159 A1 | 11/2002 |
| EP | 0347923 | 12/1989 |
| EP | 0347923 A1 | 12/1989 |
| EP | 0376763 | 7/1990 |
| EP | 0376763 A2 | 7/1990 |
| EP | 1942726 A2 | 7/2008 |

(Continued)

OTHER PUBLICATIONS

Botha, P., "Extended Donor Criteria in Lung Transplantation", Current Opinion in Organ Transplantation, 14:206-210, 2009 (5 pages).
Johnston, R., "What's Normal About DLCO?", PFT Blog, Jan. 1, 2014 (17 pages).
Chien, et al., "Functional Studies of the Heart During a 24-Hour Preservation Using a New Autoperfusion Preparation," The Journal of Heart and Lung Transplantation, 10(3):401-8 (1991) (8 pages).
Howarth, F.C. et al., "Effects of extracellular magnesium and beta adrenergic stimulation on contractile force and magnesium mobilization in the Isolated rat heart", Magnesium Research, 7:187-197, 1994 (13 pages).

(Continued)

*Primary Examiner* — Satyendra K Singh
(74) *Attorney, Agent, or Firm* — Wilmer Cutler Pickering Hale and Dorr LLP

(57) ABSTRACT

The invention, in various embodiments, provides systems, methods and solutions for perfusing an organ.

13 Claims, 6 Drawing Sheets

(56) References Cited

U.S. PATENT DOCUMENTS

| | | |
|---|---|---|
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,654,266 A * | 8/1997 | Chen et al. ............... 514/2 |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,770,149 A | 6/1998 | Raible |
| 5,776,063 A | 7/1998 | Dittrich et al. |
| 5,786,136 A | 7/1998 | Mayer |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A | 4/2000 | Rosenbaum |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,402,461 B1 | 6/2002 | Tebby |
| 6,475,716 B1 | 11/2002 | Seki |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,569,615 B1 | 5/2003 | Thatte et al. |
| 6,582,953 B2 | 6/2003 | Brasile |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,740,484 B1 * | 5/2004 | Khirabadi et al. ............ 435/1.3 |
| 6,783,328 B2 | 8/2004 | Lucke et al. |
| 6,792,309 B1 | 9/2004 | Noren |
| 6,794,124 B2 | 9/2004 | Steen |
| 6,811,965 B2 | 11/2004 | Vodovotz et al. |
| 6,878,339 B2 | 4/2005 | Akiyama et al. |
| 6,925,324 B2 | 8/2005 | Shusterman |
| 6,953,655 B1 | 10/2005 | Hassanein et al. |
| 6,974,436 B1 | 12/2005 | Aboul-Hosn et al. |
| 7,001,354 B2 | 2/2006 | Suzuki et al. |
| 7,008,380 B1 | 3/2006 | Rees et al. |
| 7,238,165 B2 | 7/2007 | Vincent et al. |
| 7,316,666 B1 | 1/2008 | Entenman et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 8,304,181 B2 | 11/2012 | Hassanein et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 8,822,203 B2 | 9/2014 | Hassanein et al. |
| 9,215,867 B2 | 12/2015 | Hassanein et al. |
| 9,457,179 B2 | 10/2016 | Hassanein et al. |
| 9,462,802 B2 | 10/2016 | Fishman et al. |
| 2001/0003652 A1 | 6/2001 | Freeman |
| 2001/0025191 A1 | 9/2001 | Montgomery |
| 2002/0012988 A1 | 1/2002 | Brasile |
| 2002/0013220 A1 | 1/2002 | Wang et al. |
| 2002/0102720 A1 | 8/2002 | Steen |
| 2002/0132220 A1 | 9/2002 | Berens et al. |
| 2002/0151950 A1 | 10/2002 | Okuzumi |
| 2002/0164795 A1 | 11/2002 | Gen |
| 2002/0177117 A1 | 11/2002 | Wolf |
| 2002/0187132 A1 * | 12/2002 | McGregor et al. ........ 424/93.21 |
| 2003/0011604 A1 | 1/2003 | Capers |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0074760 A1 | 4/2003 | Keller |
| 2003/0086830 A1 | 5/2003 | Haywood et al. |
| 2003/0135152 A1 | 7/2003 | Kollar et al. |
| 2003/0147466 A1 | 8/2003 | Liang |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0193096 A1 | 9/2004 | Cooper |
| 2004/0202993 A1 | 10/2004 | Poo et al. |
| 2004/0221719 A1 | 11/2004 | Wright et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2005/0010118 A1 | 1/2005 | Toyoda et al. |
| 2005/0019917 A1 | 1/2005 | Toledo-Pereyra et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2005/0253390 A1 | 11/2005 | Blazek |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |

(56) References Cited

U.S. PATENT DOCUMENTS

| | | |
|---|---|---|
| 2006/0154357 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0196461 A1 | 8/2007 | Weers |
| 2007/0275364 A1 | 11/2007 | Hassanein et al. |
| 2008/0017191 A1 | 1/2008 | Davies et al. |
| 2008/0017194 A1 | 1/2008 | Hassanein et al. |
| 2008/0234768 A1 | 9/2008 | Hassanein et al. |
| 2008/0286746 A1 | 11/2008 | Poo et al. |
| 2009/0142830 A1 | 6/2009 | Yamashiro et al. |
| 2009/0143417 A1 | 6/2009 | Smith et al. |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2010/0056966 A1 | 3/2010 | Toth |
| 2010/0092939 A1 | 4/2010 | Belous et al. |
| 2011/0076666 A1 | 3/2011 | Brassil |
| 2011/0136096 A1 | 6/2011 | Hassanein et al. |
| 2011/0190572 A1 | 8/2011 | Brophy et al. |
| 2011/0212431 A1 | 9/2011 | Bunegin et al. |
| 2012/0277681 A1 | 11/2012 | Kravitz et al. |
| 2013/0011823 A1 | 1/2013 | Hassanein et al. |
| 2013/0078710 A1 | 3/2013 | Hassanein et al. |
| 2013/0157248 A1 | 6/2013 | Fishman et al. |
| 2013/0295552 A1 | 11/2013 | Hassanein et al. |
| 2014/0017658 A1 | 1/2014 | Steinman et al. |
| 2014/0017660 A1 | 1/2014 | Steinman et al. |
| 2014/0135738 A1 | 5/2014 | Panian |
| 2015/0079580 A1 | 3/2015 | Hassanein et al. |
| 2015/0230453 A1 | 8/2015 | Fontes et al. |

FOREIGN PATENT DOCUMENTS

| | | |
|---|---|---|
| JP | H02-282301 A | 11/1990 |
| JP | 02-306901 A | 12/1990 |
| JP | H03-74302 A | 3/1991 |
| JP | 04-099701 A | 3/1992 |
| JP | H04-128201 A | 4/1992 |
| JP | 06-056601 | 3/1994 |
| JP | 06-305901 | 11/1994 |
| JP | 08-511012 | 11/1996 |
| JP | 2001061956 A | 3/2001 |
| JP | 2001516768 A | 10/2001 |
| JP | 2004513889 A | 5/2004 |
| JP | 2004525290 A | 8/2004 |
| JP | 2004529938 | 9/2004 |
| JP | 2004529938 A | 9/2004 |
| JP | 2008-515914 A | 5/2008 |
| JP | 2009-521931 A | 6/2009 |
| JP | 2011-511000 A | 4/2011 |
| JP | 6144238 B2 | 6/2017 |
| WO | WO-8805261 A1 | 7/1988 |
| WO | WO-9502326 A1 | 1/1995 |
| WO | WO-9531897 A1 | 11/1995 |
| WO | WO-9618293 A1 | 6/1996 |
| WO | WO-9629865 A1 | 10/1996 |
| WO | WO-9746091 A1 | 12/1997 |
| WO | WO-9915011 A1 | 4/1999 |
| WO | WO-0022927 A1 | 4/2000 |
| WO | WO-0060936 A1 | 10/2000 |
| WO | WO-0226034 A2 | 4/2002 |
| WO | WO-02/35929 A1 | 5/2002 |
| WO | WO-02089571 A1 | 11/2002 |
| WO | WO-2004026031 A2 | 4/2004 |
| WO | WO-2006042138 A2 | 4/2006 |
| WO | WO-2006076590 A2 | 7/2006 |
| WO | WO-2006124820 A2 | 11/2006 |
| WO | WO-2007079185 A2 | 7/2007 |
| WO | WO-2007124044 A2 | 11/2007 |
| WO | WO-2008106724 A1 | 9/2008 |
| WO | WO-2009/099939 A2 | 8/2009 |
| WO | WO-2009099939 | 8/2009 |
| WO | WO-2011072012 A2 | 6/2011 |
| WO | WO-2013068752 A2 | 5/2013 |
| WO | WO-2014059316 A1 | 4/2014 |
| WO | WO-2015154170 A1 | 10/2015 |

OTHER PUBLICATIONS

Moisiuk, Y. et al., "Histidine-Tryptophan-Ketoglutarate Versus Euro-Collins for Preservation of Kidneys From Non-Heart-Beating Donors," Transplantation Proceedings, 28(1):202 (1996) (1 page).

Poston, R.S. et al., "Optimizing Donor Heart Outcome After Prolonged Storage With Endothelial Function Analysis and Continuous Perfusion", Ann Thorac Surg, 78:1362-1370, 2004 (9 pages).

Shimokawa, S. et al., "A New Lung Preservation Method of Topical Cooling by Ambient Cold Air: An Experimental Study," Transplantation Proceedings, 23 (1):653-54 (1991) (2 pages).

"Glucose", The Merck Index, Entry 4535, 19th Edition, Merck & Co., INc., Rahway, NJ, pp. 699-700, 1989.

Ahmad, et al., "A Pathophysiologic Study of the Kidney Tubule to Optimize Organ Preservation Solutions", Kidney Int. 66(1):77-90 (2004).

Aitchison, et al., "Nitric Oxide During Perfusion Improves Post-transplantation Function of Non-Heart-Beating Donor Lungs", Transplantation, 75(12):1960-1964, Jun. 27, 2003, 5 pages.

Anathaswamy, Anal: "Machine keeps organs alive for longer." New Scientist.com from New Scientist Print Edition. (Aug. 16, 2001, 15:16). (http://www.newscientist.com/article.ns?id=dn1168&print=true).

Aoki, et al., "Anti-CD18 Attenuates Deleterious Effects of Cardiopulmonary Bypass and Hypothermic Circulatory Arrest in Piglets", J. Card. Surg., 10:407-417, 1995.

Associated Press: "Heart kept beating outside the body." CNN News Health Section (Oct. 7, 2001, 02:59) (CNN.com/Health with WebMD.com).

Bando, et al., "Oxygenated Perfluorocarbon, Recombinant Human Superoxide Dismutase, and Catalase Ameliorate Free Radical Induced Mycardial Injury During Heart Preservation and Transplantation", J. Tohorac Cardiovasc Surg, 96:930-938, Dec. 1988.

Barinov, et al. "Hormonal-metabolic disturbances during biological preservation of the heart," Fiziol. ZH., (Kiev), 29(3):293-299 (1983) (7 pages)—Russian Language.

Barr Laboratories, "History of Transplantation and Organ Preservation", Barr Laboratories, Inc. 2004, 4 pages.

Benichou, et al., "Canine and Human Liver Preservation for 6 to 18 Hr by Cold Infusion", Transplantation, 24(6):407-411, Dec. 1977.

Birkett, Donald J. et al: "The fatty acid content and drug binding characteristics of commercial albumin preparations." Clinica Chimerica Acts, vol. 85, pp. 253-258(1978).

Blanchard, et al., "Techniques for Perfusion and Storage of Heterotopic Heart Transplants in Mice", Microsurgery, 6:169-174, 1985.

Boggi, et al,. "Pancreas preservation with University of Wisconsin and Celsior Solutions", Transplant Proc., 36(3):563-565, 2004.

Boggi, et al., "Pancreas Preservation with University of Wisconsin and Celsior Solutions: A Single-Center, Prospective, Randomized Pilot Study", Transplantation, 77(8):186-190, 2004.

Boyle, Jr., et al., "Ischemia-Reperfusion Injury", Ann. Thorac. Surg., 64:524-530, 1997.

Brandes, H. et al. "Influence of high molecular dextrans on lung function in an ex vivo porcine lung model," J. of Surgical Research, 101:2, 225-231 (2001).

Brasile, et al., "Organ Preservation without Extreme Hypothermia Using an Oxygen Supplemented Perfusate", Art. Cells. Blood Subs. and Immob. Biotech, 22(4):1463-1468, 1994.

Burt, et al., "Myocardial Function after Preservation for 24 Hours", Jour Thorac and Cardiovascular Surgery, 92(2):238-246, 1986.

Calhoon, et al., "Twelve-Hour Canine Heart Preservation with a Simple, Portable Hypothermic Organ Perfusion Device", Ann. Thorac. Surg., 62:91-93, 1996.

(56) References Cited

OTHER PUBLICATIONS

Canelo, et al., "Experience with Hystidine Tryptophan Ketoglutarate Versus University Wisconsin Preservation Solutions in Transplantation", Int. Surg., 88(3):145-151, 2003.

Carrera, Stephen J.: "Machine may be organ transplant breakthrough." USA Today.com Health and Science (Aug. 8, 2001) (http://www.usatoday.com/news/health/2001-08-25-organ.htm).

Chambers, et al., "Lont-Term Preservation of the Heart: The Effect of Infusion Pressure During Continuous Hypothemic Cardioplegia", Jour of Heart and Lung Transp., 11(4):665-675, 1992.

Chen, et al,. "Development of New Organ Preservation Solutions in Kyoto University", Yonsei Medical Journal, 46(6):1107-1140, 2004.

Chien, et al., "A Simple Technique for Multiorgan Preservation", Journal of Thor. and Card. Surg., 95(1):55-61, 1988.

Chien, et al., "Canine Lung Transplantation after More than Twenty-Four Hours of Normothermic Preservation", J. Heart Lung Transplant., 16:3340-3351, 1997.

Christophl, et al., "A Comparison of Standard and Rapid Infusion Methods of Liver Preservation During Multi-Organ Procurement", Aust. N.Z. J. Surg, 61(9):692-694, 1991.

Cimino, Adria: "Doctor develops device to preserve donated organs." Mass High Tech, the Journal of New England Technology Online (Sep. 17, 2001) (No url), 2 pages.

Collins, "Organ Transplantation: What is the State of the Art?", Ann. Surg., 238(6 Suppl.):S72-S89, 2003.

Cronin, David et al: "Liver Transportation at the University of Chicago." Clinical Transplants, Ch. 21, pp. 231-237 (1991).

Daemen, et al., "Short-Term Outcome of Kidney Transplants from Non-Heart-Beating Donors after Preservation by Machine Perfusion", Transpl Int., 9(Suppl. 1):S76-S80, 1996.

Demertzis, et al., "University of Wisconsin Versus St. Thomas' Hospital Solution for Human Donor Heart Preservation", Ann. Thorac. Surg., 55:1131-1137, 1993.

Den Butter, et al., "Comparison of Solutions for Preservation of the Rabbit Liver as Tested by Isolation Perfusion", Transpl. Int., 8(6):466-471, 1995.

Denham, et al., "Twenty-Four Hour Canine Renal Preservation by Pulsatile Perfusion", Hypothermic Storage, and Combinations of the Two Methods, Transplant Proc., 9(3):1553-1556, 1977.

Dobrian, et al., "In Vitro Formation of Exidatively-Modified and Reassembled Human Low-Density Lipoproteins", Biochimica et Biophysica Acta (BBA), 1169:12-24, 1993.

Dow Jones and Company: "The Nation: warm-storage devices may aid organ transplants." Dow Jones Publication Library, Aug. 26, 2001, 1 page.

Drexler, et al., "Effect of L-Arginine on Coronary Endothelial Function in Cardiac Transplant Recipients", Circulation, 89(4):1615-1623, 1994.

Eiseman, et al., "A Disposable Liver Perfusion Chamber", Surgery, 6:1163-1166, 1966.

Engelman, et al., "Influence of Steroids on Complement and Cytokine Generation After Cardiopulmonary Bypass", Ann. Thorac. Surg., 60(3):801-804, 1995.

European Search Report for European Patent Application No. 08795820.3 dated Apr. 17, 2014. 6 pages.

European Search Report for European Patent Application No. 09707471.0 dated May 27, 2014. 7 pages.

European Search Report issued in EP12770852.7, dated Sep. 23, 2014, 8 pages.

Fabregas, Lisa: "UPMC tests machine to aid heart transplants." Pittsburgh Tribune Review Live.com (Feb. 24, 2002) (http://www.pittsburghlive.com/x/pittsburghtrib/print_19181.html).

Faggian, et al., "Donor Organ preservation in High-Risk Cardiac Transplantation", Transplant Proc., 36:617-619, 2004.

Featherstone et al. "Comparison of Phosphodiesterase Inhibitors of Differing Isoenzyme Selectivity Addes to St. Thomas Hospital Cardioplegic Solution Used for Hypothermic Preservation of Rat Lungs." Am. J. Respir. Crit. Care Med. Mar. 2000. 162(3):850-856.

Fehrenberg, et al., "Protective Effects of B2 Preservation Solution in Comparison to a Standard Solution (Histidine-Tryptophan-Ketoglutarate/Bretschneider) in a Model of Isolated Autologous Hemopherfused Porcine Kidney", Nephron Physiol, 96:52-58, 2004.

Ferrera, et al., "Comparison of Different Techniques of Hypothermic Pig Heart Preservation", Ann. Thorac. Surg., 57(5):1233-1239, 1994.

File History for U.S. Appl. No. 60/616,835, filed Oct. 7, 2004. 82 pages.

File History for U.S. Appl. No. 60/694,971, filed Jun. 28, 2005. 280 pages.

File History for U.S. Appl. No. 60/725,168, filed Oct. 6, 2005. 699 pages.

Finn, et al., "Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass", J. Thorac. Cardiovasc. Surg., 111(2):451-459, 1996.

Forcade, et al., "A New Method of Kidney Preservation with Collins' Solution", Biomed., 21(7):308-311, 1974.

Fraser, et al., "Evaluation of Current Organ Preservation Method for Heart-Lung Transplantation", Transplant. Proc., 201(1 Suppl):987-990, 1988.

Grynberg et al. "Fatty acid oxidation in the heart," Journal of Cardiovascular Pharmacology, 28(Suppl. 1):S11-S17 (1996) (8 pages).

Guarrera, et al., "Pulsatile Machine Perfusion with Vasosol Solution Improves Early Graft Function after Cadaveric Renal Transplantation", Transplantation, 77(8):1264-1268, 2004.

Gundy, et al., "Successful Thransplantation of Hearts Harvested 30 Minutes after Death from Exsanguination", Ann. Thorac. Surg., 53(5):772-775, 1992.

Habazetti, et al., "Improvement in Functional Recovery of the Isolated Guinea Pig Heart after Hyperkalemic Reperfusion with Adenosine", J. Thorac. Cardiovasc. Surg., 111(1):74-84, 1996.

Hachida, et al., "Abstract: Efficacy of Myocardial Preservation using HTK Solution in Continuous 120 Min Cross-Clamping Method—a Comparative Study with GIK Method", Nippon Kyobu Geka Gakkai Zasshi, 41(9):1495-1501, 1993.

Hardesty et al. Original Communications, "Autoperfusion of the heart and lungs for preservation during distant procurement," J. Thorac. Cardiovasc. Surg., 93:11-18 (1987) (8 pages).

Hartman, "The Role of Bradykinin and Nitric Oxide in the Cardiopulmonary Bypass and Hypothermic Circulatory Arrest in Piglets", J. Card. Surg., 10:407-417, 1995.

Hassanein, et al., "Continuous Perfusion of Donor Hearts in the Beating State Extends Preservation Time and Improves Recovery of Function", The Journal of Thoracic and Cardiovascular Surgery, 116:821-830, 1998.

Hassanein, Waleed et al: "A novel approach for 12 hour donor heart preservation." Cardio-Thoracic and Vascular Surgery: Transplantation and Ventricular Assistance, Abstract 2080, 70th Scientific Session Cardio-Thoracic and Vascular Surgery: Transplantation and Ventricular Assistance, Circulation 96(8):I-372, 1997, 1 page.

Heil, et al., "A Controlled Comparison of Kidney Preservation by Two Methods: Machine Perfusion and Cold Storage", Transplant. Proc., 19(1):2046, 1987.

Hülsmann et al. "Loss of cardiac contractility and severe morphologic changes by acutely lowering the pH of the perfusion medium: protection by fatty acids," BBAGEN 20256, Biochimica et Biophysica Acta., 1033:214-218 (1990) (5 pages).

Imber, et al., "Advantages of Normothermic Perfusion Over Cold Storage in Liver Preservation", Transplantation, 73(5):701-709, 2002.

International Search Report and Written Opinion for International Application No. PCT/US12/33626 dated Sep. 20, 2012. 13 pages.

International Search Report for PCT/US07009652 dated Apr. 18, 2008.

Janssen, et al., "UW is Superior to Celsior an dHTK in the Protection of Human Liver Endothelial Cells Against Preservation Injury", Liver Transpl., 10(12):1514-1523, 2004.

(56) References Cited

OTHER PUBLICATIONS

Katz, Robert et al. "Physics, CHapter 9: Hydrodynamics (Fluids in Motion)." Hydrodynamics. University of Nebraska—Lincoln. Pap143. No Month Listed 1958. 18 pages.

Kawamura, et al., "Long-Term Preservation of Canine Pancreas by a New Simple Cold Storage Method using Perfluorochemical—The Two-Layer Cold Storage Method (Euro-Collins' Solution/Perfluorochemical)", Kobe J. Med. Sci., 38(2):135-145, 1992.

Kelly, "Current Strategies in Lung Preservation", J. Lab. Clin. Med., 136:427-440, 2000.

Keshavjee, et al., "A Method for Safe Twelve-Hour Pulmonary Preservation", J. Thorac Cardiovasc Surg, 96:529-534, 1989.

Kioka, et al., "Twenty-Four-Hour Isolated Heart Preservation by Perfusion Method with Oxygenated Solution Containing Perfluorochemicals and Albumin", J. Heart Transplant, 5:437-443, 1986.

Klatz, Richard: "Machine keeps human kidney alive for 24-hours." The World Health Network Anti-Aging and Longevity (Aug. 25, 2001) (http://www.worldhealth.net/p/393,1313.htm).

Kozaki, et al., "Usefulness of a Combination of Machine Perfusion and Pentoxifylline for Porcine Liver Transplantation from Non-Heart-Beating Donors with Prolonged Hypotension", Transplant Proc., 29:3476-3477, 1997.

Kuroda, et al., "A New, Simple Method for Cold Storage of the Pancreas Using Perfluorochemical", Transplantation, 46(3):457-460, 1988.

Lasley, et al,, "Protective Effects of Adenosine in the Reversibly Injured Heart", Ann. Thorac. Surg., 60(3):843-846, 1995.

Lawrence, Curtis: "Machine Preserves Organs Outside Body." Chicago Sun-Times Health Section Online (Nov. 4, 2001) (no url listed), 1 page.

Lefer, et al., "Attenuation of Myocardial Ischemia-Reperfusion Injury with Nitric Oxide Replacement Therapy", Ann. Thorac. Surg., 60(3):789-792, 1995.

Li, et al., "Functional Recovery in Rabbit Heart after Preservation with a Blood Cardiplegic Solution and Perfusion", J. Heart Lung Transplant, 12(2):263-270, 1993.

Li, et al., "Insulin in University of Wisconsin Solution Exacerbates the Ischemic Injury and Decreases the Graft Survival Rate in Rat Liver Transplantation", Transplantation, 76(1):44-49, Jul. 15, 2003.

Li, et al., "Insulin in UW Solution Exacerbates Hepatic Ischemia/Reperfusion Injury by Energy Depletion Through the IRS-2/SREBP-1C Pathway", Liver Transpl., 10(9):1173-1182, 2004.

Liu, et al., "Annexin V Assay-Proven Aitn-Apoptotic Effect of Ascorbic Acid 2-glucoside after Cold Ischemia/Reperfusion Injury in Rat Liver Transplantation", Acta Med. Okayama, 57(5):209-216, 2003.

Macchiarini, P. et al. "Ex vivo lung model of pig-to-human hyperacute xenograft rejection," J. of Thoracic and Cardiovascular Surgery, 114:3, 315-325 (2000).

Mankad, et al., "Endothelial Dysfunction Caused by University of Wisconsin Preservation Solution in the Rat Heart", J. Thorac. Cardiovasc. Surg., 104(6):1618-1624, 1992.

Matsuno, et al., "Effectiveness of Machine Perfusion Preservation as a Viablility Determination Method for Kidneys Procured from Non-Heart-Beating Donors", Transplant. Proc., 26(4):2421-2422, 1994.

Matsuno, et al., "The Effect of Machine Perfusion Preservation versus Cold Storage on teh Function of Kidneys from Non-Heart-Beating Donors", Transplantation, 57(2):293-294, 1994.

Menasche, "The Inflammatory Response to Cardiopulmonary Bypass and its Impact on Postoperative Myocaridal Function", Curr. Opin. Cardiology, 10:597-604, 1995.

Menasche, et al., "Experimental Evaluation of Celsior, a New Heart Preservation Solution", Eur. J. Cardiothor. Surg., 8:207-213, 1989.

Menasche, et al., "Improved Recovery of Heart Transplants with a Specific Kit of Preservation Solutions", J. THorac. Cardiovasc., Surg., 105(2):353-363, 1993.

Moller-Pedersen, et al., "Evaluation of Potential Organ Culture Media for Eye Banking Using Human Donor Corneas", Br. J. Opthamol., 85(9):1075-1079, 2001.

Morimoto, et al., "A Simple Method for Extended Heart-Lung Preservation by Autoperfusion", Trans. Am. Soc. Aftif. Intern Organs, 30:320-324, 1984.

Nicholson, et al., "A Comparison of Renal Preservation by Cold Storage and Machine Perfusion Using a Porcine Autotransplant Model", Transplantation, 78(3):333-337, 2004.

No Author Listed, "Human Heart Beats on its Own Outside Body", USA Today, Oct. 6, 2001, 1 page.

No Author Listed, "Human Heart Kept Alive Outside Body for First Time in Study of Portable Organ Preservation System at University of Pittsburgh Medical Center", McGowan Institute for Regenerative Medicine, 2001, 2 pages.

No Author Listed, "Machine Keeps Human Kidney Alive for 24-Hours", reported by www.ap.org, Aug. 25, 2001, accessed via http://www.worldhealth.net/p/393.1313.html, date accessed Jul. 5, 2006, 1 page.

No Author Listed, "Machine May be Organ Transplant Breakthrough", USA Today, Aug. 25, 2001, 1 page.

No Author Listed. "Custodiol HTK." Physicians' Desk Reference. 57th Edition, Thomson PDR. ISBN:1-56363-445-7. No Month Listed—2003. 3 pages.

No Author Listed. "SOLTRAN Kidney Perfusion Fluid." Baxter. No Month Listed—2001-2004. 1 page.

No Author Listed. "UW Solution Composition." Date Unknown. 1 page.

No Author Listed: "Human heart kept alive outside body for first time in Study of Portable Organ Preservation System at University of Pittsburgh Medical Center." (Oct. 7, 2001) (http://www.upmc.com/Communications/MediaRelations/NewsReleaseArchives/By+/T/Transplantation/Pops.htm).

No Author Listed, "New discovery in organ transplantation." MSNBC Chicago (2001) (www.nbc5.com), 1 page.

Odagiri, et al., "New Pulsatile Pump Using Assist Device—Hemodynamic Comparison of Pulsatile V-A Bypass (VABP), Pulsatile Left Heart Bypass (LHBP) and Constant Flow Left Heart Bypass (LHB)", Journal of Japan Surgical Society, 83(6):515-523, Jun. 1982, English Abstract Only, 12 pages.

Opelz, et al., "Comparative Analysis of Kidney Preservation Methods. Collaborative Transplant Study", Transplant Proc., 28(1):87-90, 1996.

Opetz, et al., "Advantage of Cold Storage over Machine Perfusion for Preservation of Cadaver Kidneys", Transplantation, 33(1):64-68, 1982.

Ota, et al., "Artificial Organ—Current State and Future of Substitution of Functions", pp. 150-151, No Month Listed, 1983, 7 pages—English translation.

PCT/US08/61454 International search report dated Dec. 5, 2008 (2 pages).

PCT/US09/032619 International Search report, dated Jun. 4, 2009 (4 pages).

PCT/US98/19912 International search report dated May 3, 1999 (4 pages).

Pearl, et al., "Loss of Endothelium-Dependent Vasodilation and Nitric Oxide Release after Myocardial Protection with University of Wisconsin Solution", J. Thorac. Cardiovasc., Surg., 107(1):257-264, 1994.

Petrovsky, et al., "Justification and Application of a New Method for Transorganic Oxygen Preservation of the Kidneys", Vestn Akad Med Nauk SSSR, 2:69-82, 1989.

Pinsky, et al., "Restoration of the cAMP Second Messenger Pathway Enhances Cardiac Preservation for Transplantation in a Heterotopic Rat Model", J. Clin. Invest., 92(6):2944-3002, 1993.

Ploeg, et al., "Successful 72-Hour Cold Storage of Dog Kidneys with UW Solution", Transplantation, 46(2):191-196, 1988.

Pokorny, et al., "Histidine-Tryptophan-Ketoglutarate Solution for Organ Preservation in Human Liver Transplantation—a Prospective Multi-Center Observation Study", Translp Int., 17(5):256-260, 2004.

(56) References Cited

OTHER PUBLICATIONS

Potdar, et al., "Initial Experience Using Histidine-Tryptophan-Ketoglutarate Solution in Clinical Pancreas Transplantation", Clin. Transplant., 18(6):661-665, 2004.
Pozniak, Alexa: "Keeping Hearts Alive, Doctors Develop a High-Tech System to Salvage Donated Organs." Boston ABCNews.com (Dec. 7, 2001) (http://abcnews.go.com/print?id=117085).
Probst et al. "Carbohydrate and fatty acid metabolism of cultured adult cardiac myocytes," Am. J. Physiol. 250 (Heart, Circ. Physiol. 19):H853-H860 (1986) (8 pages).
Rao, et al., "Donor Blood Perfusion Improves Myocardial Recovery After Heart Transplantation", J. Heart Lung Transplant., 16(6):667-673, 1997.
Reddy, et al., "Preservation of Porcine Non-Heart Beating Donor Livers by Sequential Cold Storage and Warm Perfusion", Transplantation, 77(9):1328-1332, 2004.
Richens, et al., "Clinical Study of Crystalloid Cardioplegia vs Aspartate-Enriched Cardioplegia Plus Warms Reperfusion for Donor Heart Preservation", Transplant. Proc., 24(1):1608-1610, 1993.
Rinder, et al., "Blockade of C5a and C5b-9 Generatin Inhibits Leukocyte and Platelet Activation during Extracorporeal Circulation", J. Clin. Invest., 96:1564-1572, Sep. 1995.
Rosenkranz, et al., "Substrate Enhancement of Cardioplegic Solution: Experimental Studies and Clinical Evaluation", Ann. THorac. Surg., 60:797-800, 1995.
Rossi, Lisa: "New organ preservation solution easier to use." Innovations Report (Feb. 2, 2003) (http://www.innovations-report.com/html/reports/medicine_report-18854.html).
S.A.S.; "Investigations: Warm storage for donor organs." The University of Chicago Magazine Online (2001) (no url listed), 1 page.
Sangstat, the Transplant Company: "Celsior, Cold Storage Solution." Sangstat Medical Corporation and Fresenius Kabi France. Aug. 1999, 5 pages.
Sato, et al., "Supplemental L-Arginine During Cardioplegic Arrest and Reperfusion Avoids Regional Postischemic Injury", J. Thorac. Cardiovasc. Surg., 110(2):302-314, 1995.
Schimokawa, et al., "A New Lung Preservation Method of Topical Cooling by Ambient Cold Air Combined with High-Frequency Oscilation: An Experimental Study", Transplant. Proc., 26(4):2364-2366, 1994.
Schmid, et al., "Th eUse of Myocytes as a Model for Developing Successful Heart Preservation Solutions", Transplantation, 52(1):20-26, Jul. 1991.
Schon, et al., "Liver Transplantation after Organ Preservation with Normothemic Extracorporeal Perfusion", Ann. Surg., 233(1):114-123, 2001.
Schwalb, et al., "New Solution for Prolonged Myocardial Preservation for Transplantation", J. Heart Lung Transplant., 17(2):222-229, 1998.
No Author Listed, "2002 Design & Engineering Awards: Portable organ preservation system. TransMedics, Inc.", Science, (2002), 1 page.
Seccombe, et al., "Coronary Artery Endothelial Function After Myocardial Ischemia and Reperfusion", Ann. Thorac. Cardiovasc. Surg., 60(2):778-788, 1995.
Segal, et al., "Posttransplantation Function of Hearts Preserved with Fluorochemical Emulsion", J. Heart Lung Transplant., 13(4):669-680, 1994.
Segel, et al., "Recovery of Sheep Hearts after Perfusion Preservation in Static Storage with Crystalloid Media", The Journal of Heart and Lung Transplantation, 17:211-221, 1998.
Shirakura, et al., "Multiorgan Procurement from Non-Heart-Beating Donors by use of Osaka Universkty Cocktail, Osaka Rinse Solution, and the Portagle Cardiopulmonary Bypass Machine", Transplant. Proc., 25(6):3093-3094, 1993.
Southard, Dr. James: "The Right Solution for Organ Preservation." Business Briefing: Global Surgery, Department of Surgery, University of Wisconsin, pp. 79-84, 2004, 6 pages.
Steen, et al., "Transplantation of Lungs from Non-Heart-Beating Donors after Functional Assessment Ex Vivo", Annals of Thoracic Surgery, 76:244-252, 2003, 11 pages.
Stubenitsky, et al., "Kidney Preservation in the Next Millenium", Transpl Int., 12:83-91, 1999.
Sunamori, et al., "Relative Advantages of Nondepolarizing Solution to Depolarizing University of Wisconsin Solution in Donor Heart Preservation", Transplant. Proc., 25(1):1613-1617, 1993.
Tang, et al., "Warm Ischemia Lung Protection with Pinacidil: an ATP Regulated Potassium Channel Opener", Ann Thorac Surg, 76:385-389, 2003.
Tesi, et al., "Pulsatile Kidney Perfusion for Preservation and Evaluation: Use of High-Risk Kidney Donors to Expand the Donor Pool", Transplant Proc., 25(6):3099-3100, 1993.
The Associated Press: "Human heart beats on its own outside body." (Oct. 6, 2001) (http://www.usatoday.com/news/health/2001-10-06-heart.htm).
The University of Wisconsin Board of Regents: "Formula for Belzer MPS Solution." The University of Wisconsin (Oct. 3, 2003) (http://www.surgery.wisc.edu/transplant/research/southard/BelzerMPS.shtml).
Turpin, et al., "Perfusion of Isolated Rat Adipose Cells," The Journal of Clinical Investigation, 60:442-448 (1977), 7 pages.
ViaSpan (Belzer UW) Cold Storage Solution, Data Sheet, Barr Laboratories, Inc., May 2002, 2 pages.
Vinten-Johnsen, et al., Reduction in Surgical Ischemic-Reperfusion Injury with Adenosine and Nitric Oxide Therapy, Ann. Thorac. Surg., 60(3):852-857, 1995.
Voiglio, E. et al. "Rat multiple organ blocks: microsurgical technique of removal for ex vivo aerobic organ preservation using a fluorcarbon emulsion," Microsurgery 20:3, 109-115 (2000).
Watanabe, et al., "Effects of Free Fatty Acids on the Binding of Bovine and Human Serum Albumin with Steroid Hormones", Biochimica et Biophysica Acta (BBA), 1289:385-396, 1996.
Wicomb, et al., "24-Hour Rabbit Heart Storage with UW Solution", Transplantation, 48(1):6-9, 1989.
Wicomb, et al., "Cardiac Transplantation Following Storage of the Donor Heart by a Portable Hypothermic Perfusion System", The Annals of Thoracic Surgery, 37(3):243-248, 1984.
Wicomb, et al., "Orthotopic Transplantation of the Babook Heart After 20 to 24 Hours Preservation by Continuous Hypothermic Perfusion with an Oxygenated Hyperosmolar Solution", The Journal of Thoracic and Cardiovascular Surgery, 83(1):133-140, 1982.
Wright, N. et al. "A porcine ex vivo paracorporeal model of lung transplantation," Laboratory Animals, 34:1, 56-62 (2000).
Yland, et al., "New Pulsatile Perfusion Method for Non-Heart-Beating Cadaveric Donor Organs: A Preliminary Report", Transplantation Proceedings, 25(6):3087-3090, 1993.
Zhang, et al., "Research Progress on Preservation of Severed Limbs", Chinese JOurnal of Reparative and Reconstructive Surgery, 14(3):189-192, 2000.
Zhengquang, et al., "A Study on the Preservation of Rat Kidney with HX-III Solution", WCUMS 31(3):347-349, 2000.
Carrier, B., "Chapter 4: Hypoxia and Oxygenation", Alaska Air Medical Escort Training Manual, Fourth Edition, pp. 71-82, 2006, 12 pages.
Definition of Examine, Merriam-Webster Dictionary on-line. www.merriam-webster.com/dictionary/examine, Printed Feb. 9, 2011, (1 page).
Egan, T. M. et al., "Ex Vivo Evaluation of Human Lungs for Transplant Suitability", Ann Thorac Surg, vol. 81, No. 4, pp. 1205-1213 (Apr. 2006) (9 pages).
Synchrony Definition, http://dictionary.reference.com/browse/synchrony, Random House Unabridged Dictionary, 2006 (1 page).
Yeung, J. C., et al., "Physiologic assessment of the ex vivo donor lung for transplantation", The Journal of Heart and Lung Transplantation, 31(10):1120-1126, Oct. 2012 (7 pages).
Chinchoy, Edward Cheng-wey; "The Development, Refinement, and Uses of a Physiologically Working Isolated Ex Vivo Swine Heart Model", A thesis submitted to the Faculty of the Graduate School of the University of Minnesota, Dec. 1999 (136 pages).

(56) References Cited

OTHER PUBLICATIONS

Johnson, Kerry et al, "POPS: Portable Organ Preservation System", UPMC Health System and TransMedics, Inc. (No date given) (1 page).
U.S. Food and Drug Administration, Center for Drug Evaluation and Research, "Drugs@FDA-Solu-Medrol: Label and Approval History", (Available online at http://www.accessdata.fda.gov/scripts/cder/drugsatfda/index.cfm?fuseaction=Search.Label_ApprovalHistory#apphist . . . ), accessed Feb. 9, 2010 (3 pages).
U.S. Food and Drug Administration, Center for Drug Evaluation and Research, "Drugs@FDA-Solu-Medrol: Drug Details", (Accessible online at http://www.accessdata.fda.gov/scripts/cder/drugsatfda/index.cfm?fuseaction=Search.DrugDetails . . . ), accessed Feb. 9, 2010 (1 page).
Kubono, K. et al., "Examination of Plasma and Corpuscle Adenosine Concentration in Normal Subject by Radioimmunoassay", Rinshou Kagaku (Clinical Chemistry, 20(2):72-77, Jun. 1991 (6 pages)—Japanese Language.
Sekine, M. et al., "Effect of Obese and Aging on Blood Fatty Acid Consumption in Japanese", Bulletin of the Graduate School of Human Life Science, Showa Women's University, 4:63-70, 1995 (8 pages)—English Abstract.
Yokoyama, H. et al., "Isolated Dog Hearts Prepared in Cold Tyrode Solution and Reperfused with Arterial Blood Are Functionally and Ultrastructurally Normal", The Tohoku Journal of Experimental Medicine, 156:121-134, 1988 (14 pages).
International Search Report and Written Opinion issued by the U.S. Patent and Trademark Office as Searching Authority, in International Application No. PCT/US16/50512, dated Dec. 12, 2016 (9 pages).
Extended European Search Report issued in European Application No. 17172411.5, dated Nov. 8, 2017 (7 pages).

\* cited by examiner

SYSTEMS, METHODS, COMPOSITIONS AND SOLUTIONS FOR PERFUSING AN ORGAN

REFERENCE TO RELATED APPLICATIONS

This application claims the benefit of U.S. patent application Ser. No. 11/246,919, filed on Oct. 7, 2005; U.S. Provisional Patent Application Ser. No. 60/694,971, filed on Jun. 28, 2005; and U.S. Provisional Patent Application Ser. No. 60/725,168, filed on Oct. 6, 2005, and entitled Systems and Methods for Ex-Vivo Organ Care. The specifications of each of the foregoing are incorporated by reference herein in their entirety.

FIELD

The invention relates generally to organ perfusion. In various illustrated embodiments the invention provides for systems, methods, compositions and solutions for perfusing an organ.

BACKGROUND

Many patients need organ transplants but are unable to obtain suitable organs. One of the primary reasons is that organs that are otherwise viable when harvested from a donor are not preserved for long enough periods of time to allow them to be transported to appropriate recipients. With current preservation techniques, transplantable organs remain viable for about three to four hours and, beyond that time, suffer ischemia and tissue injury, which renders them unviable for transplant.

Current preservation techniques include cryopreservative methods, which involve the cooling of the transplantable organ to temperatures well below physiological temperatures (e.g., below 25° C.). Such techniques typically use preservation solutions that do not replenish energy sources within the organ during transplant or maintain the organ in a functioning state and therefore are largely ineffective in preventing ischemia and other injuries to the organ. The solutions also often rely on the use of high molecular weight impermeants to maintain the organ at these temperatures prior to transplantation, and such components are in many cases harmful to the organ.

Although improvements to solutions have been made over the last several years, particularly as disclosed in U.S. Pat. Nos. 6,100,082, 6,046,046, and PCT application PCT/US98/19912, further improvements are still needed.

SUMMARY

The invention addresses deficiencies in the art by providing, in various embodiments, improved systems, methods, compositions and solutions for perfusing an organ prior to transplantation. According to one aspect, the solutions include components adapted to preserving and maintaining a harvested organ ex-vivo in its functioning state under physiologic or near physiologic conditions prior to its transplantation, while minimizing reperfusion injury and ischemia to the organ while awaiting transplantation.

According to another feature, the solutions include energy sources for the organ while it is being prepared for and undergoing transplantation. Energy sources include, for example, one or more of carbohydrate sources, components for synthesis of energy-rich molecules, such as phosphate sources, and other components. According to one embodiment, the solutions provide for amino acids for assisting the organ in cellular protein synthesis during perfusion. According to one embodiment, the solutions also provide components that help maintain the organ's normal functionality during perfusion, such as cardio stimulants, insulin and other hormones, electrolytes, etc. The solutions may also be adapted to include drugs or other therapeutics for preservation of the organ and/or patient care.

In another aspect, the invention provides for systems and methods for improved delivery of preservation. In certain embodiments the solutions are combined with blood products for perfusion. The solutions, systems and methods are also adaptable to drug delivery systems. In certain embodiments, the solutions are combined with additional additives at the point of use.

In one embodiment, a composition for use in a solution for perfusing an organ, such as a heart, is provided comprising one or more carbohydrates, one or more organ stimulants, and a plurality of amino acids that do not include asparagine, glutamine, or cysteine.

In another embodiment, a system for perfusing an organ, such as a heart, is provided comprising an organ and a substantially cell-free composition, where the compositions comprises one or more carbohydrates, one or more organ stimulants, and a plurality of amino acids that do not include asparagine, glutamine, or cysteine.

BRIEF DESCRIPTION OF THE FIGURES

The foregoing and other objects and advantages of the invention will be appreciated more fully from the following further description thereof, with reference to the accompanying figures wherein.

DETAILED DESCRIPTION

Figure 1:
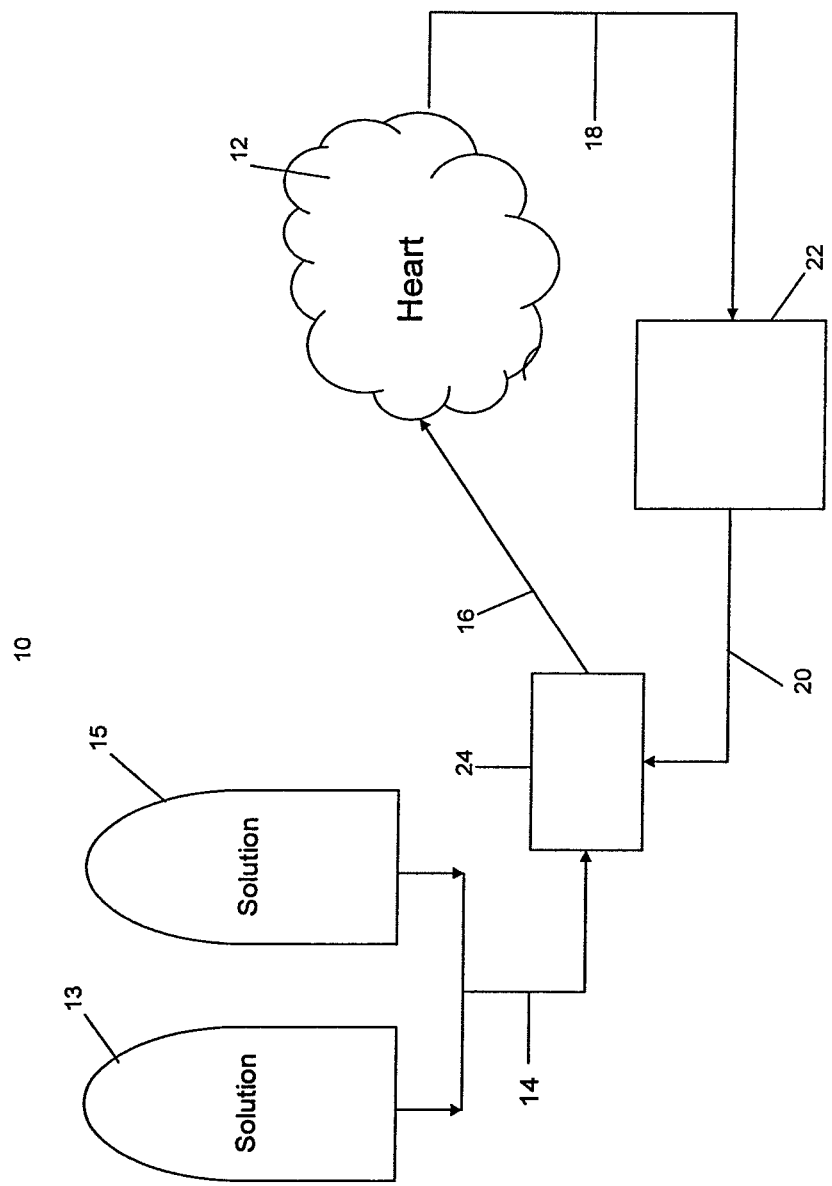
FIG. 1 depicts an embodiment of a perfusion system using two solutions for maintaining a heart.

The invention addresses deficiencies in the prior art by providing in various illustrated embodiments systems, methods, compositions, and solutions for maintaining an organ in a functioning state ex vivo under physiological or near physiological conditions. In one embodiment, the organ is a heart and is maintained in a beating state at a physiologic or near physiologic temperature during perfusion of a perfusion fluid, which may include one or more of the solutions described herein. According to certain embodiments, solutions with particular solutes and concentrations are selected and proportioned to enable the organ to function at physiologic or near physiologic conditions. For example, such conditions include maintaining organ function at or near a physiological temperature and/or preserving an organ in a state that permits normal cellular metabolism, such as protein synthesis.

In certain embodiments solutions are formed from compositions by combining components with a fluid, from more concentrated solutions by dilution, or from more dilute solutions by concentration. In exemplary embodiments, suitable solutions include one or more energy sources, one or more stimulants to assist the organ in continuing its normal physiologic function prior to and during transplantation, and one or more amino acids selected and proportioned so that the organ continues its cellular metabolism during perfusion. Cellular metabolism includes, for example conducting protein synthesis while functioning during perfusion. Some illustrative solutions are aqueous based, while other illustrative solutions are non-aqueous, for example organic solvent-based, ionic-liquid-based, or fatty-acid-based.

The solutions may include one or more energy-rich components to assist the organ in conducting its normal physiologic function. These components may include energy rich materials that are metabolizable, and/or components of such materials that an organ can use to synthesize energy sources during perfusion. Exemplary sources of energy-rich molecules include, for example, one or more carbohydrates. Examples of carbohydrates include monosaccharides, disaccharides, oligosaccharides, polysaccharides, or combinations thereof, or precursors or metabolites thereof. While not meant to be limiting, examples of monosaccharides suitable for the solutions include octoses; heptoses; hexoses, such as fructose, allose, altrose, glucose, mannose, gulose, idose, galactose, and talose; pentoses such as ribose, arabinose, xylose, and lyxose; tetroses such as erythrose and threose; and trioses such as glyceraldehyde. While not meant to be limiting, examples of disaccharides suitable for the solutions include (+)-maltose (4-O-(α-D-glucopyranosyl)-α-D-glucopyranose), (+)-cellobiose (4-O-(β-D-glucopyranosyl)-D-glucopyranose), (+)-lactose (4-O-(β-D-galactopyranosyl-β-D-glucopyranose), sucrose (2-O-(α-D-glucopyranosyl-β-D-fructofuranoside). While not meant to be limiting, examples of polysaccharides suitable for the solutions include cellulose, starch, amylose, amylopectin, sulfomucopolysaccharides (such as dermatane sulfate, chondroitin sulfate, sulodexide, mesoglycans, heparan sulfates, idosanes, heparins and heparinoids), and glycogen. In some embodiments, monossacharides, disaccharides, and polysaccharides of both aldoses, ketoses, or a combination thereof are used. One or more isomers, including enantiomers, diastereomers, and/or tautomers of monossacharides, disaccharides, and/or polysaccharides, including those described and not described herein, may be employed in the solutions described herein. In some embodiments, one or more monossacharides, disaccharides, and/or polysaccharides may have been chemically modified, for example, by derivatization and/or protection (with protecting groups) of one or more functional groups. In certain embodiments, carbohydrates, such as dextrose or other forms of glucose are preferred.

Other possible energy sources include adenosine triphosphate (ATP), co-enzyme A, pyruvate, flavin adenine dinucleotide (FAD), thiamine pyrophosphate chloride (co-carboxylase), β-nicotinamide adenine dinucleotide (NAD), β-nicotinamide adenine dinucleotide phosphate (NADPH), and phosphate derivatives of nucleosides, i.e. nucleotides, including mono-, di-, and tri-phosphates (e.g., UTP, GTP, GDF, and UDP), coenzymes, or other bio-molecules having similar cellular metabolic functions, and/or metabolites or precursors thereof. For example, phosphate derivatives of adenosine, guanosine, thymidine (5-Me-uridine), cytidine, and uridine, as well as other naturally and chemically modified nucleosides are contemplated.

In certain embodiments, one or more carbohydrates is provided along with a phosphate source, such as a nucleotide. The carbohydrate helps enable the organ to produce ATP or other energy sources during perfusion. The phosphate source may be provided directly through ATP, ADP, AMP, or other sources. In other illustrative embodiments, a phosphate is provided through a phosphate salt, such as glycerophosphate, sodium phosphate or other phosphate ions. A phosphate may include any form thereof in any ionic state, including protonated forms and forms with one or more counter ions.

The solutions may include one or more organ stimulants for assisting the organ's normal physiologic function during perfusion. In some illustrative embodiments, where the transplanted organ is a heart, cardio stimulants are provided to enable the heart to continue functioning (e.g., continue beating) during perfusion and transplantation. Such stimulants may include, for example, catecholamines, such as epinephrine and/or norepinephrine, which facilitate beating of the heart. Other cardio stimulants may be used, such as certain forms of peptides and/or polypeptides (e.g., vasopressin, Anthropleurin-A and Anthropleurin-B), and/or β1/β2-adrenoreceptor blocking agents (such as CGP 12177), buplinarol, pindolol, alprenolol, and cardiac glycosides. One or more natural products may also be used, such as digitalis (digoxin), palustrin, and/or ferulic acid. Stimulants such as those mentioned above can be included with the solutions or added at the point of use by the user.

In some instances, additional components are provided to assist the organ in conducting its metabolism during perfusion. These components include, for example, forms or derivatives of adenine and/or adenosine, which may be used for ATP synthesis, for maintaining endothelial function, and/or for attenuating ischemia and/or reperfusion injury. According to certain implementations, a magnesium ion source is provided with a phosphate, and in certain embodiments, with adenosine to further enhance ATP synthesis within the cells of the perfused organ.

As noted, the solution may include one or more amino acids, preferably a plurality of amino acids, to support protein synthesis by the organ's cells. Suitable amino acids include, for example, any of the naturally-occurring amino acids. The amino acids may be, in various enantiomeric or diastereomeric forms. For example, solutions may employ either D- or L-amino acids, or a combination thereof, i.e. solutions enantioenriched in more of the D- or L-isomer or racemic solutions. Suitable amino acids may also be non-naturally occurring or modified amino acids, such as citrulline, ornithine, homocystein, homoserine, β-amino acids such as β-alanine, amino-caproic acid, or combinations thereof.

Certain exemplary solutions include some but not all naturally-occurring amino acids. In some embodiments, solutions include essential amino acids. For example, a solution may be prepared with one or more or all of the following amino-acids:

Glycine
Alanine
Arginine
Aspartic Acid
Glutamic Acid
Histidine
Isoleucine
Leucine
Methionine
Phenylalanine -continued Proline
Serine
Thereonine
Tryptophan
Tyrosine
Valine
Lysine acetate In certain embodiments, non-essential and/or semi-essential amino acids are not included in the solutions. For example, in some embodiments, asparagine, glutamine, and/or cysteine are not included. In other embodiments, the solution contains one or more non-essential and/or semi-essential amino acids. Accordingly, in other embodiments, asparagine, glutamine, and/or cysteine are included.

The solutions may also contain electrolytes, particularly calcium ions for facilitating enzymatic reactions, cardiac contractility, and/or coagulation within the organ. Other electrolytes may be used, such as sodium, potassium, chloride, sulfate, magnesium and other inorganic and organic charged species or combinations thereof. It should be noted that any component provided hereunder may be provided, where valence and stability permit, in an ionic form, in a protonated or unprotonated form, in salt or free base form, or as ionic or covalent substituents in combination with other components that hydrolyze and make the component available in aqueous solutions, as suitable and appropriate.

In certain embodiments, the solutions contain buffering components. For example, suitable buffer systems include 2-morpholinoethanesulfonic acid monohydrate (MES), cacodylic acid, $H_2CO_3$/$NaHCO_3$ ($pK_{a1}$), citric acid ($pK_{a3}$), bis(2-hydroxyethyl)-imino-tris-(hydroxymethyl)-methane (Bis-Tris), N-carbamoylmethylimidino acetic acid (ADA), 3-bis[tris(hydroxymethyl)methylamino]propane (Bis-Tris Propane) ($pK_{a1}$), piperazine-1,4-bis(2-ethanesulfonic acid) (PIPES), N-(2-Acetamido)-2-aminoethanesulfonic acid (ACES), imidazole, N,N-bis(2-hydroxyethyl)-2-aminoethanesulfonic acid (BES), 3-(N-morpholino)propanesulphonic acid (MOPS), $NaH_2PO_4$/$Na_2HPO_4$ ($pK_{a2}$), N-tris(hydroxymethyl)methyl-2-aminoethanesulfonic acid (TES), N-(2-hydroxyethyl)-piperazine-N'-2-ethanesulfonic acid (HEPES), N-(2-hydroxyethyl)piperazine-N'-(2-hydroxypropanesulfonic acid) (HEPPSO), triethanolamine, N-[tris(hydroxymethyl)methyl]glycine (Tricine), tris hydroxymethylaminoethane (Tris), glycineamide, N,N-bis(2-hydroxyethyl) glycine (Bicine), glycylglycine ($pKa2_{a2}$), N-tris (hydroxymethyl)methyl-3-aminopropanesulfonic acid (TAPS), or a combination thereof. In some embodiments, the solutions contain sodium bicarbonate, potassium phosphate, or TRIS buffer.

The solutions may include other components to help maintain the organ and protect it against ischemia, reperfusion injury and other ill effects during perfusion. In certain exemplary embodiments these components may include hormones (e.g., insulin), vitamins (e.g., an adult multivitamin, such as multi-vitamin MVI-Adult™), and/or steroids (e.g., dexamethasone and SoluMedrol™).

In another aspect, a blood product is provided with the solution to support the organ during metabolism. Exemplary suitable blood products may include whole blood, and/or one or more components thereof such as blood serum, plasma, albumin, and red blood cells. In embodiments where whole blood is used, the blood may be passed through a leukocyte and platelet depleting filter to reduce pyrogens, antibodies and/or other items that may cause inflammation in the organ. Thus, in some embodiments, the solution employs whole blood that has been at least partially depleted of leukocytes and/or whole blood that has been at least partially depleted of platelets.

The solutions are preferably provided at a physiological temperature and maintained thereabout throughout perfusion and recirculation. As used herein, "physiological temperature" is referred to as temperatures between about 25° C. and about 37° C., for example, between about 30° C. and about 37° C., such as between about 34° C. and about 37° C.

Table 1 sets forth components that may be used in a preservative solution for preserving an organ as described herein.

TABLE 1

Component of Exemplary Composition for a Preservative Solution

| Component | Exemplary Concentration Ranges in a preservative solution |
|---|---|
| Alanine | about 1 mg/L-about 10 g/L |
| Arginine | about 1 mg/L-about 10 g/L |
| Asparagine | about 1 mg/L-about 10 g/L |
| Aspartic Acid | about 1 mg/L-about 10 g/L |
| Cysteine | about 1 mg/L-about 10 g/L |
| Cystine | about 1 mg/L-about 10 g/L |
| Glutamic Acid | about 1 mg/L-about 10 g/L |
| Glutamine | about 1 mg/L-about 10 g/L |
| Glycine | about 1 mg/L-about 10 g/L |
| Histidine | about 1 mg/L-about 10 g/L |
| Hydroxyproline | about 1 mg/L-about 10 g/L |
| Isoleucine | about 1 mg/L-about 10 g/L |
| Leucine | about 1 mg/L-about 10 g/L |
| Lysine | about 1 mg/L-about 10 g/L |
| Methionine | about 1 mg/L-about 10 g/L |
| Phenylalanine | about 1 mg/L-about 10 g/L |
| Proline | about 1 mg/L-about 10 g/L |
| Serine | about 1 mg/L-about 10 g/L |
| Threonine | about 1 mg/L-about 10 g/L |
| Tryptophan | about 1 mg/L-about 10 g/L |
| Tyrosine | about 1 mg/L-about 10 g/L |
| Valine | about 1 mg/L-about 10 g/L |
| Adenine | about 1 mg/L-about 10 g/L |
| ATP | about 10 ug/L-about 100 g/L |
| Adenylic Acid | about 10 ug/L-about 100 g/L |
| ADP | about 10 ug/L-about 100 g/L |
| AMP | about 10 ug/L-about 100 g/L |
| Ascorbic Acid | about 1 ug/L-about 10 g/L |
| D-Biotin | about 1 ug/L-about 10 g/L |
| Vitamin D-12 | about 1 ug/L-about 10 g/L |
| Cholesterol | about 1 ug/L-about 10 g/L |
| Dextrose (Glucose) | about 1 g/L-about 150 g/L |
| Multi-vitamin Adult | about 1 mg/L-about 20 mg/L or 1 unit vial |
| Epinephrine | about 1 ug/L-about 1 g/L |
| Folic Acid | about 1 ug/L-about 10 g/L |
| Glutathione | about 1 ug/L-about 10 g/L |
| Guanine | about 1 ug/L-about 10 g/L |
| Inositol | about 1 g/L-about 100 g/L |
| Riboflavin | about 1 ug/L-about 10 g/L |
| Ribose | about 1 ug/L-about 10 g/L |
| Thiamine | about 1 mg/L-about 10 g/L |
| Uracil | about 1 mg/L-about 10 g/L |
| Calcium Chloride | about 1 mg/L-about 100 g/L |
| NaHCO$_3$ | about 1 mg/L-about 100 g/L |
| Magnesium sulfate | about 1 mg/L-about 100 g/L |
| Potassium chloride | about 1 mg/L-about 100 g/L |
| Sodium glycerophosphate | about 1 mg/L-about 100 g/L |
| Sodium Chloride | about 1 mg/L-about 100 g/L |
| Sodium Phosphate | about 1 mg/L-about 100 g/L |
| Insulin | about 1 IU-about 150 IU |
| Serum albumin | about 1 g/L-about 100 g/L |
| Pyruvate | about 1 mg/L-about 100 g/L |
| Coenzyme A | about 1 ug/L-about 10 g/L |
| Serum | about 1 ml/L-about 100 ml/L |
| Heparin | about 500 U/L-about 1500 U/L |
| SoluMedrol™ | about 200 mg/L-about 500 mg/L |

TABLE 1-continued

Component of Exemplary Composition for a Preservative Solution

| Component | Exemplary Concentration Ranges in a preservative solution |
|---|---|
| Dexamethasone | about 1 mg/L-about 1 g/L |
| FAD | about 1 ug/L-about 10 g/L |
| NADP | about 1 ug/L-about 10 g/L |
| adenosine | about 1 mg/L-about 10 g/L |
| guanosine | about 1 mg/L-about 10 g/L |
| GTP | about 10 ug/L-about 100 g/L |
| GDP | about 10 ug/L-about 100 g/L |
| GMP | about 10 ug/L-about 100 g/L |

The solutions described herein may be prepared from compositions having one or more components such as those described above in concentrations such as those described above. An exemplary embodiment of a composition adaptable for use in organ perfusion includes one or more components selected from Table 2. The amounts provided describe preferred amounts relative to other components in the table and may be scaled to provide compositions of sufficient quantity. In some embodiments, the amounts listed in Table 2 can vary by ±about 10% and still be used in the solutions described herein.

TABLE 2

Component of Exemplary Composition for a Preservative Solution

| Component | Amount |
|---|---|
| Adenosine | about 675 mg-about 825 mg |
| Calcium Chloride dihydrate | about 2100 mg-about 2600 mg |
| Glycine | about 315 mg-about 385 mg |
| L-Alanine | about 150 mg-about 200 mg |
| L-Arginine | about 600 mg-about 800 mg |
| L-Aspartic Acid | about 220 mg-about 270 mg |
| L-Glutamic Acid | about 230 mg about 290 mg |
| L-Histidine | about 200 mg-about 250 mg |
| L-Isoleucine | about 100 mg about 130 mg |
| L-Leucine | about 300 mg-about 380 mg |
| L-Methionine | about 50 mg-about 65 mg |
| L-Phenylalanine | about 45 mg-about 60 mg |
| L-Proline | about 110 mg-about 140 mg |
| L-Serine | about 80 mg-about 105 mg |
| L-Thereonine | about 60 mg-about 80 mg |
| L-Tryptophan | about 30 mg-about 40 mg |
| L-Tyrosine | about 80 mg-about 110 mg |
| L-Valine | about 150 mg-about 190 mg |
| Lysine Acetate | about 200 mg-about 250 mg |
| Magnesium Sulfate Heptahydrate | about 350 mg-about 450 mg |
| Potassium Chloride | about 15 mg-about 25 mg |
| Sodium Chloride | about 1500 mg-about 2000 mg |
| Dextrose | about 25 g-about 120 g |
| Epinephrine | about 0.25 mg-about 1.0 mg |
| Insulin | about 75 Units-about 150 Units |
| MVI-Adult ™ | 1 unit vial |
| SoluMedrol ™ | about 200 mg-about 500 mg |
| Sodium Bicarbonate | about 10-about 25 mEq |

A solution may be prepared combining components selected by a user with an aqueous fluid to form a preservative solution. In an illustrative embodiment, one or more components from Table 2 are combined in the relative amounts listed therein per about 1000 mL of aqueous fluid to form a preservative solution for perfusing an organ, such as a heart. In some embodiments the quantity of aqueous fluid can vary ±about 10%.

In another aspect, solutions may be administered in combinations as desired by a medical operator. FIG. 1 is a conceptual diagram of a system 10 for perfusing a heart 12 according to an illustrative embodiment of the invention. As shown, the illustrative system 10 includes two solutions, a first solution 13 and a second solution 15, which are joined through fluid line 14 and become part of a perfusion circuit that includes lines 16, 18 and 20. The fluid lines interconnect a perfusion operating system 22 and a mixing chamber 24, with solutions 13 and 15 to perfuse the heart 12. In some embodiments, the system 10 is sterilized prior to use. In operation, the solutions 13 and 15 feed to the mixing chamber 24 via the conduit 14. Solutions 13 and 15 mix with a perfusion fluid that circulates in the perfusion circuit. The perfusion fluid may be blood or synthetic blood based. Perfusion fluid recirculates from the heart 12 via the fluid conduit 18, the perfusion operating system 22, and the fluid conduit 20 to the mixing chamber 24. There the recirculated fluid is mixed with solutions 13 and 15 and fed to the heart via the conduit 16. Since the heart 12 is maintained in a beating state, it continues to received fluid from the conduit 16 and feed it back via the conduit 18 for remixing in the mixing chamber 24.

Figure 2:
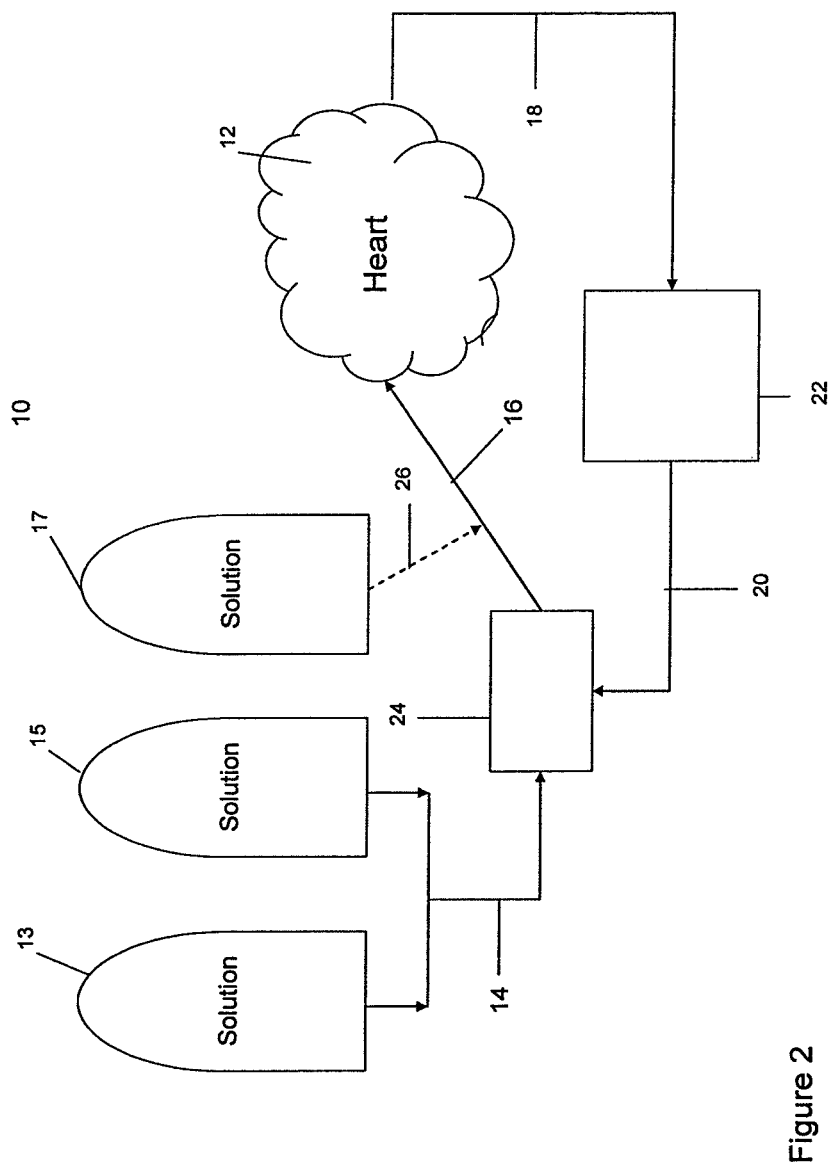
FIG. 2 depicts an embodiment of a perfusion system using two solutions and also a priming solution.

FIG. 2 is another conceptual drawing depicting a further illustrative embodiment of the perfusion system 10. As shown, the illustrative embodiment of FIG. 2 includes a priming solution 17 applied to the system prior to addition of a perfusion fluid. As shown in FIG. 2, the priming solution 17 flows into line 26 to provide the priming solution 17 to the system prior to perfusing the heart 12 with a perfusion fluid containing solutions 13 and 15. The priming solution 17 may include, for example, any or all of the components included in the solutions 13 and 15.

Figure 3:
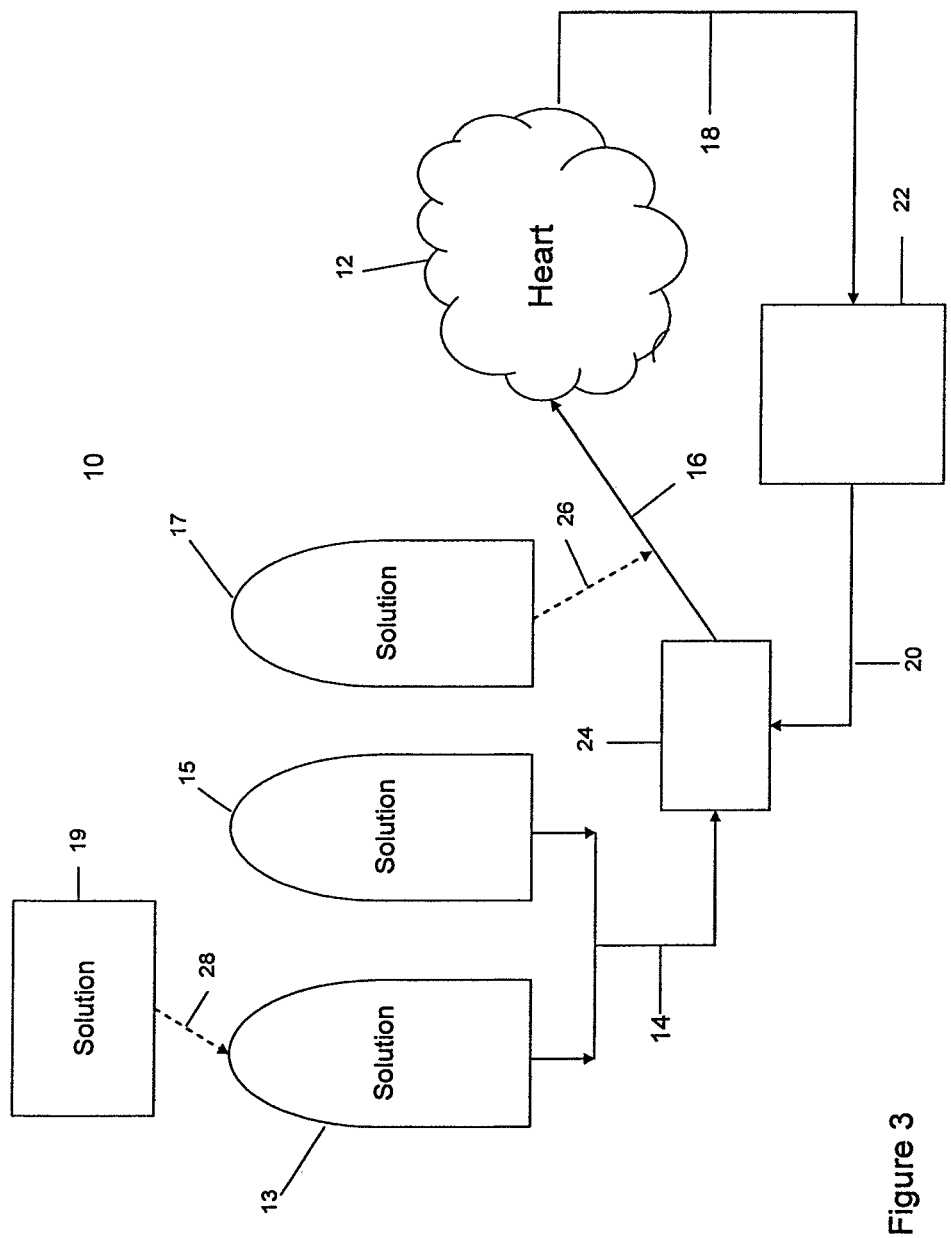
FIG. 3 depicts an embodiment of a perfusion system using two solutions, a priming solution, and a composition or solution having sensitive material added prior to perfusion.

In other illustrative embodiments, the solutions 15 and/or 17 may be provided systematically to optimize the effectiveness of the system. For example, as shown in FIG. 3, the solution 13 may include a composition or solution 19, which may include components that are sensitive to sterilization and other techniques used to prepare the solution 13 for perfusion. For example, the composition or solution 19 may include insulin or other bio-components, organic compounds, and/or biological molecules that would decompose or degrade when sterilized, such as via an autoclave. In this instance, as shown in FIG. 3, the composition or solution 19 may be added to the solution 13 prior to or during perfusion of the donor organ. As shown in FIG. 3, the composition or solution 19 may be applied to the solution 13 through a fluid conduit 28. The composition or solution 19 may also be applied to fluid conduit 14 (though not shown in FIG. 3), and then mixed with the perfusion fluid in chamber 24 just prior to application to the conduit 16.

In some illustrative embodiments, the solutions described herein are combined with a blood product, such as whole blood or components thereof, which may also be oxygenated, to give a perfusion fluid. Additionally, synthetic blood products may be used as a substitute or in combination with blood products. Such combined solutions may be included in a perfusion circuit, such as those shown in FIGS. 1 to 3.

In other illustrative embodiments, one of the composition or solutions 13, 15, 17, or 19 may include one or more organ stimulants, such as cardio stimulants, and/or other components. The other components may include, for example, adenosine, a magnesium ion source, one or more phosphates, calcium ions, etc. In embodiments utilizing two or more solutions, such as those in FIGS. 1 to 3, the solution 15 may include one or more carbohydrates and may also include a phosphate source. According to some illustrative embodiments, the perfusion fluid includes more than one composition or solution 13, 15, 17 or 19 to avoid precipitation of calcium phosphate in embodiments where calcium ions and phosphate ions are used.

In one embodiment, a maintenance solution is made from the combination of a first solution, substantially formed from one or more amino acids, and a second solution, substantially formed from one or more carbohydrates, such as dextrose or glucose. The maintenance solution may also have additives, such as those described herein, administered at the point of use just prior to infusion into the organ perfusion system. For example, additional additives that can be included with the solution or added at the point of use by the user include hormones and steroids, such as dexamethasone and insulin, as well as vitamins, such as an adult multi-vitamin, for example adult multivitamins for infusion, such as MVI-Adult™. Additional small molecules and large bio-molecules may also be included with the solution or added at the point of use by the user, for example, therapeutics and/or components typically associated with blood or blood plasma, such as albumin.

In some embodiments, therapeutics that may be included in the compositions, solutions, and systems described herein include hormones, such as thyroid hormones, for example $T_3$ and/or $T_4$ thyroid hormones. Further therapeutics that may be included include drugs such as anti-arrhythmic drugs, for example, for heart therapy, and beta blockers. For instance, in certain embodiments, one or more thyroid hormones, one or more anti-arrhythmic drugs, and one or more beta blockers are added to the first solution, the second solution, and/or the maintenance solution either before or during perfusion of the organ. The above therapeutics may also be added directly to the system, for example to the perfusion circuit before or during perfusion of the organ.

Table 3 sets forth an exemplary first solution, comprising a tissue culture media having the components identified in Table 3 and combined with an aqueous fluid, which may be used as to perfuse an organ as described herein. The amounts of components listed in Table 3 are relative to each other and to the quantity of aqueous solution used. In some embodiments, about 500 mL of aqueous fluid is used. In other embodiments about 1 L of aqueous fluid is used. For example, combination of about 500 mL of first solution with 500 mL of second solution affords a maintenance solution of about 1 L. In some embodiments, the quantity of aqueous solution can vary ±about 10%. The component amounts and the quantity of aqueous solution may be scaled as appropriate for use. The pH of the first solution, in this embodiment, may be adjusted to be about 7.0 to about 8.0, for example about 7.3 to about 7.6.

TABLE 3

Composition of Exemplary First Solution
(about 500 mL aqueous solution)

| Tissue Culture Component | Amount | Specification |
| --- | --- | --- |
| Adenosine | 750 mg | ±about 10% |
| Calcium Chloride dihydrate | 2400 mg | ±about 10% |
| Glycine | 350 mg | ±about 10% |
| L-Alanine | 174 mg | ±about 10% |
| L-Arginine | 700 mg | ±about 10% |
| L-Aspartic Acid | 245 mg | ±about 10% |
| L-Glutamic Acid | 258 mg | ±about 10% |
| L-Histidine | 225 mg | ±about 10% |
| L-Isoleucine | 115.5 mg | ±about 10% |
| L-Leucine | 343 mg | ±about 10% |
| L-Methionine | 59 mg | ±about 10% |
| L-Phenylalanine | 52 mg | ±about 10% |
| L-Proline | 126 mg | ±about 10% |
| L-Serine | 93 mg | ±about 10% |
| L-Thereonine | 70 mg | ±about 10% |
| L-Tryptophan | 35 mg | ±about 10% |

TABLE 3-continued

Composition of Exemplary First Solution
(about 500 mL aqueous solution)

| Tissue Culture Component | Amount | Specification |
| --- | --- | --- |
| L-Tyrosine | 92 mg | ±about 10% |
| L-Valine | 171.5 mg | ±about 10% |
| Lysine Acetate | 225 mg | ±about 10% |
| Magnesium Sulfate Heptahydrate | 400 mg | ±about 10% |
| Potassium Chloride | 20 mg | ±about 10% |
| Sodium Chloride | 1750 mg | ±about 10% |

Since amino acids are the building blocks of proteins, the unique characteristics of each amino acid impart certain important properties on a protein such as the ability to provide structure and to catalyze biochemical reactions. The selection and concentrations of the amino acids provided in the first solution provide support of normal physiologic functions such as metabolism of sugars to provide energy, regulation of protein metabolism, transport of minerals, synthesis of nucleic acids (DNA and RNA), regulation of blood sugar and support of electrical activity, in addition to providing protein structure. Additionally, the concentrations of specific amino acids found in the first solution can be used to predictably stabilize the pH of the first solution and/or other solutions and fluids to which the first solution may be added, for example the maintenance solution and/or the perfusion fluid.

Table 4 provides an exemplary second solution 15, comprising a solution which may be used with the systems of FIGS. 1-3. The second solution 15 includes dextrose and an aqueous solvent. In some embodiments, the second solution 15 further includes sodium glycerol phosphate. The amount of components in Table 5 is relative to the amount of aqueous solvent (about 500 mL) and may be scaled as appropriate. In some embodiments, the quantity of aqueous solvent varies ±about 10%.

TABLE 4

Components of Exemplary Second Solution (about 500 mL)

| Component | Amount | Specification |
| --- | --- | --- |
| Dextrose | 40 g | ±about 10% |

Additional components may be included in the first or second solution, the maintenance solution, and/or the priming solution and may include one or more of those set forth in Table 5. These additional or supplemental components may be added individually, in various combinations, or all at once as a composition. For example, in certain embodiments, the epinephrine, insulin, and MVI-Adult™, listed in Table 5, are added to the maintenance solution. In another example, the SoluMedrol™ and the sodium bicarbonate, listed in Table 5, are added to the priming solution. The additional components may also be combined in one or more combinations or all together and placed in solution before being added to the first or second solution or to the maintenance solution. These additional components may be degraded or otherwise inactivated if subjected to sterilization, and, as such, may be appropriately applied directly to the perfusion circuit or to a first 13 or second 15 solution after sterilization, such as described with regard to the composition or solution 19 of FIG. 3. In some embodiments, dexamethasone may also be added to solutions described herein. The component amounts listed in Table 5 are relative to each other and to the amounts of components in Table 3, Table 4 and/or Table 6 and/or to the amount of aqueous solution used in the first or second solution, the maintenance solution, or the priming solution and may be scaled as appropriate for the amount required.

TABLE 5

Exemplary Supplemental Components Added Prior to Use

| Component | Amount | Type | Function | Specification |
|---|---|---|---|---|
| Epinephrine | about 0.50 mg | Catecholamine Hormone | Maintains Vascular Tone, Basal Catecholamine Levels for Cardiac Function | ±about 10% |
| Insulin | about 100 Units | Hormone | Facilitates Glucose Absorption | ±about 10% |
| MVI-Adult ™ | 1 unit vial | Vitamin | Source of antioxidants | ±about 10% |
| SoluMedrol ™ | about 250 mg in about 4 mL water | Steroid | | ±about 10% |
| Sodium Bicarbonate | about 20 mEq | Buffer | Maintains pH | ±about 10% |

As described above, in certain illustrative embodiments, solutions are used to perfuse an organ prior to transplantation. In certain embodiments one or more solutions are applied to maintain the organ, and a separate solution is applied to prime the organ prior to applying one or more maintenance solutions. Certain exemplary components for priming solutions are identified in Table 6. In some embodiments, the priming solutions includes one or more carbohydrates. The component amounts in Table 6 are relative to each other and to the amount of aqueous solvent (about 500 mL) and may be scaled as appropriate. In certain embodiments, the quantity of aqueous solvent varies ±about 10%.

TABLE 6

Composition of Exemplary Priming Solution
(about 500 mL aqueous solution)

| Component | Amount | Specification |
|---|---|---|
| Mannitol | 12.5 g | ±about 10% |
| Sodium Chloride | 4.8 g | ±about 10% |
| Potassium Chloride | 185 mg | ±about 10% |
| Magnesium Sulfate heptahydrate | 185 mg | ±about 10% |
| Sodium Glycerophosphate | 900 mg | ±about 10% |

In some illustrative embodiments, the invention combines solutions as described herein in desired sequences to provide for improved physiological performance of the organ. Although the first and second solutions are shown above, and referenced as solutions 13 and 15 in FIGS. 1-3, the solutions may be divided into any number of solutions, their positions interchanged in system 10, and applied in any manner necessary to maintain the functioning organ.

In some illustrative embodiments, the solutions contemplated herein may be adapted for use with an organ perfusion system such as that described in U.S. Pat. Nos. 6,100,082 or 6,046,046, or PCT application PCT/US98/19912, the specifications of which are hereby incorporated by reference in their entirety.

Certain embodiments of the first solution include epinephrine and a plurality of amino acids. In certain embodiments, the first solution includes electrolytes, such as calcium and magnesium. The first solution may also include other components such as adenosine and/or one or more components from Table 3. In certain embodiments a second solution includes one or more carbohydrates and may also include a phosphate source. The second solution is typically maintained at a pH of about 5.0 to about 6.5, for example of about 5.5 to about 6.0.

In certain embodiments methods for perfusing an organ are provided through the use of solutions described herein, such as through the systems illustrated in FIGS. 1 to 3. As shown in the figures, perfusion may occur through a beating organ and may take place at physiological temperature. In certain embodiments the methods include providing a fluid for perfusing the organ, the fluid including a phosphate source, one or more organ stimulants, such as epinephrine, and one or more carbohydrates. In certain embodiments the fluid may be perfused through the organ and the organ is maintained in a beating state without the use of an applied vasopressor to effect the circulation of the fluid. In some embodiments, the organ is a heart.

In one illustrative embodiment, the system described in FIGS. 1-3 is used to perfuse an organ. In this embodiment, the system has a port for a priming solution that includes the priming solution shown in Table 6, a first chamber that contains a first solution having the components described above in Table 3, a port for a supplemental composition or solution having the components described in Table 5, and a second chamber containing a second solution having the components shown in Table 4. The priming solution may also be contained in a third chamber. The first solution, second solution, and the priming solution are sterilized through an autoclave, for example, to a sterility assurance level of about $10^{-6}$, then the supplemental composition or solution is added to the first solution. The perfusion system is then primed with the priming solution for about 10 minutes. In some embodiments, the priming is through perfusion in the direction of normal flow of fluid through the organ. In other embodiments, the priming is through retrograde perfusion, i.e., having a flow direction that is counter directional to the normal flow of fluid through the organ. After priming, the remaining solutions are combined and infused into the perfusion system at a flow-rate selected to replace necessary substrates as they are consumed by the organ. In some embodiments, the flow rate approximates physiologic fluid flow through the organ. Fluid flow rates during heart priming are about 1 L/min, while solution infusion rates during heart perfusion are about 10 mL/hr to about 40 mL/hr. Optionally, an additional solution containing a blood product is provided through which the blood product is combined with the circulating fluid and used to perfuse the organ.

In one embodiment, a composition for use in a solution for perfusing an organ, such as a heart, is provided comprising one or more carbohydrates, one or more organ stimulants, and a plurality of amino acids that do not include asparagine, glutamine, or cysteine. The composition may also include other substances, such as those used in solutions described herein.

In another embodiment, a system for perfusing an organ, such as a heart, is provided comprising an organ and a substantially cell-free composition, comprising one or more carbohydrates, one or more organ stimulants, and a plurality of amino acids that do not include asparagine, glutamine, or cysteine. Substantially cell-free includes systems that are substantially free from cellular matter; in particular, systems that are not derived from cells. For example, substantially cell-free includes compositions and solutions prepared from non-cellular sources.

In another aspect, the solutions and systems may be provided in the form of a kit that includes one or more organ maintenance solutions. An exemplary maintenance solution may include components identified above in one or more fluid solutions for organ perfusion. In certain embodiments, the maintenance solution may include multiple solutions, such as a first solution and a second solution and/or a supplemental composition or solution, or may include dry components that may be regenerated in a fluid to form one or more solutions for organ perfusion. The kit may also comprise one or more concentrated solutions which, on dilution, provide a first, second, and/or supplemental solution as described herein. The kit may also include a priming solution. In an exemplary embodiment, the maintenance solution includes a first solution and second solution such as those described above, and a priming solution such as that described above.

In certain embodiments, the kit is provided in a single package, wherein the kit includes one or more solutions (or components necessary to formulate the one or more solutions by mixing with an appropriate fluid), and instructions for sterilization, flow and temperature control during perfusion and use and other information necessary or appropriate to apply the kit to organ perfusion. In certain embodiments, a kit is provided with only a single solution (or set of dry components for use in a solution upon mixing with an appropriate fluid), and the single solution (or set of dry components) is provided along with a set of instructions and other information or materials necessary or useful to operate the solution in a perfusion apparatus or system.

In another aspect, the systems, solutions and methods may be used to deliver therapeutics to an organ during perfusion. For example, one or more of the solutions and/or systems described above may include one or more drugs, biologics, gene therapy vectors, or other therapeutics which are delivered to the organ during perfusion. Suitable exemplary therapeutics may include drugs, biologics, or both. Suitable drugs may include, for example, anti fungals, anti-microbials or anti-biotics, anti-inflammatories, anti-proliferatives, anti-virals, steroids, retinoids, NSAIDs, vitamin D3 and vitamin D3 analogs, calcium channel blockers, complement neutralizers, ACE inhibitors, immuno-suppressants, and other drugs. Suitable biologics may include proteins; suitable biologics may also include vectors loaded with one or more genes for gene therapy application.

For example, suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable anti-viral agents include but are not limited to trifluridine, cidofovir, acyclovir, penciclovir, famciclovir, valcyclovir, gancyclovir, and docosanol.

Suitable human carbonic anhydrase inhibitors include but are not limited to methazoliamide, acetazolamide, and dorzolamide.

Suitable anti-proliferative agents include but are not limited to 5-FU, taxol, daunorubicin, and mitomycin.

Suitable antibiotic (antimicrobial) agents include but are not limited to bacitracin, chlorhexidine, chlorhexidine digluconate, ciprofloxacin, clindamycin, erythromycin, gentamicin, lomefloxacin, metronidazole, minocycline, moxifloxacin, mupirocin, neomycin, ofloxacin, polymyxin B, rifampicin, ruflozacin, tetracycline, tobramycin, triclosan, and vancomycin. The antiviral and antibacterial prodrugs described herein may be used to treat appropriately responsive systemic infections.

Figure 4:
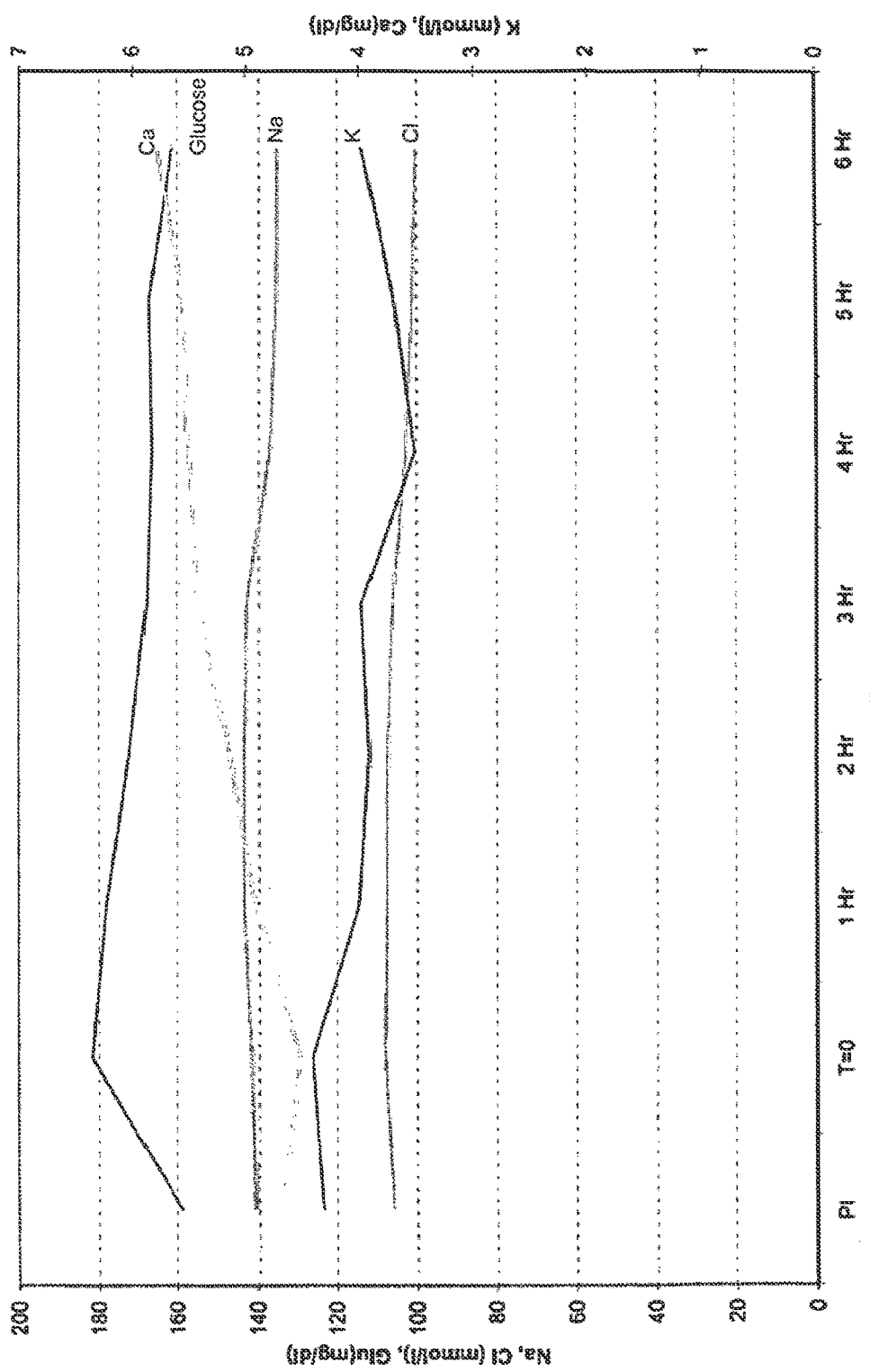
FIG. 4 depicts a chart demonstrating electrolyte stability for an organ under going perfusion according to an embodiment of the invention.

Certain experimental data are available to describe certain embodiments of the solutions described herein and their use in organ perfusion. Certain data are set for in FIGS. 4-6. FIG. 4 depicts a chart demonstrating electrolyte stability for an organ under going perfusion according to an embodiment of the invention. In the embodiment associated with FIG. 4, the organ is a heart wherein perfusion is conducted analogous to physiological conditions; i.e. a solution as described herein is perfused in the typical physiological direction out of the aorta. The rate of perfusion is approximately 30 mL/hr. As can be seen from FIG. 4, the levels of various electrolytes: sodium, potassium, calcium, and chloride ions, as well as dissolved glucose, remain at stable levels throughout the course of perfusion, from before the organ is connected to the perfusion system (the pre-instrumentation (PI) period) to six hours after connection of the organ.

Figure 5:
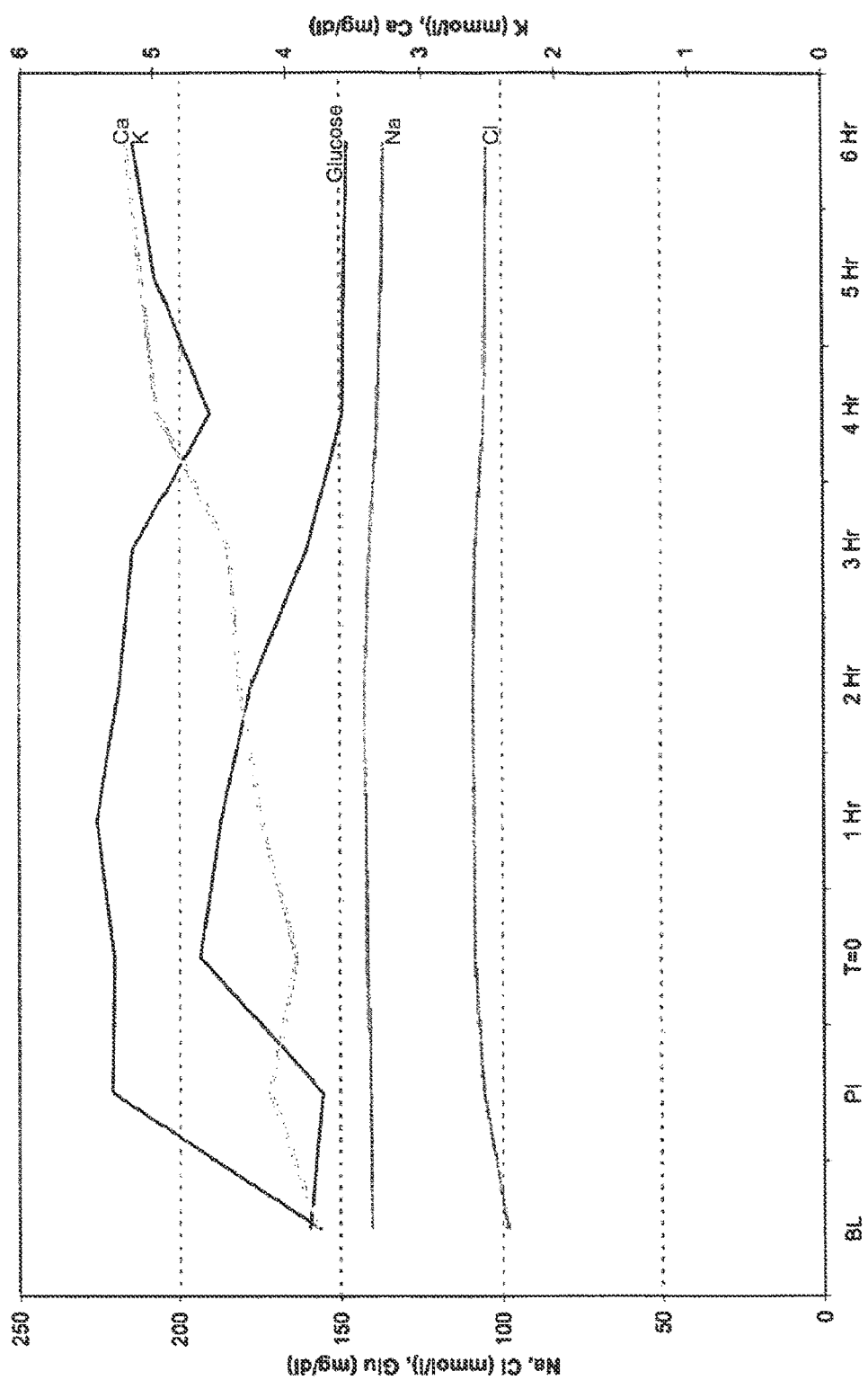
FIG. 5 depicts a chart demonstrating electrolyte stability for an organ under going perfusion according to another an embodiment of the invention.

FIG. 5 depicts a chart demonstrating electrolyte stability for an organ under going perfusion according to another embodiment of the invention. In the embodiment associated with FIG. 5, the organ is a heart wherein perfusion is conducted, in one respect, in an atypical fashion from physiological conditions; that is, a solution as described herein is perfused in the reverse physiological direction into the aorta. Such a retrograde perfusion perfuses the coronary sinus. In some embodiments, the left side of the heart remains empty. The rate of perfusion is approximately 30 mL/hr. As can be seen from FIG. 5, the levels of various electrolytes: sodium, potassium, calcium, and chloride ions, as well as dissolved glucose, remain at stable levels throughout the course of perfusion, from before the organ is connected to the perfusion system (the pre-instrumentation (PI) period) to six hours after connection of the organ. FIG. 5 also demonstrates that the levels of the electrolytes and glucose remain at levels similar to those for the base line (BL) normal physiological state for the organ.

Figure 6:
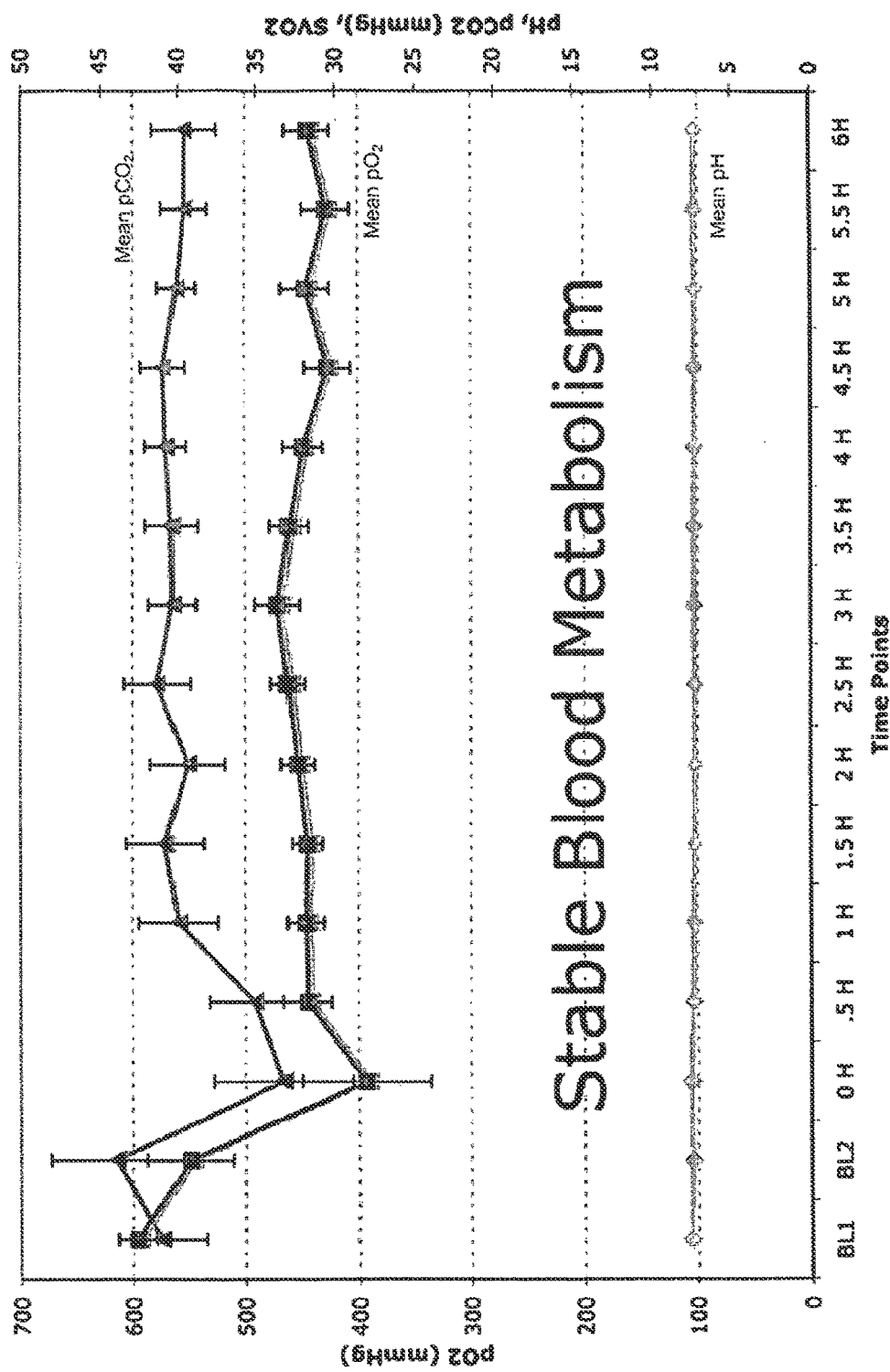
FIG. 6 depicts a chart demonstrating the arterial blood gas profile for an organ under going perfusion according to an embodiment of the invention.

FIG. 6 depicts a chart demonstrating the arterial blood gas profile for an organ under going perfusion according to another embodiment of the invention. As can be seen from FIG. 6, the levels of various blood gasses: carbon dioxide and oxygen, and pH remain at stable levels throughout the six hour course of perfusion. FIG. 6 also demonstrates that the levels of carbon dioxide, oxygen, and pH remain at levels similar to those for two base line (BL) measurements for the normal physiological state for the organ. FIGS. 4-6 demonstrate the ability of the present systems and methods to maintain an organ under stable physiological or near physiological conditions.

This application incorporates by reference the specification from each of the following applications: U.S. application Ser. No. 09/534,092, filed on Mar. 23, 2000, PCT/US98/19912, filed on Sep. 23, 1998, U.S. application Ser. No. 09/054,698 filed on Apr. 3, 1998, and U.S. application Ser. No. 08/936,062 filed on Sep. 23, 1997.

It is to be understood that while the invention has been described in conjunction with the detailed description thereof, the forgoing description is intended to illustrate and not limit the scope of the invention, which is defined by the scope of the appended claims. For example, a variety of systems and/or methods may be implemented based on the disclosure and still fall within the scope of the invention. Other aspects, advantages, and modifications are within the scope of the following claims.

What is claimed is:

1. A perfusion system configured for maintaining an ex-vivo heart in a functioning state under physiological or near physiological conditions comprising:
   a first chamber containing a first solution comprising one or more cardio stimulants selected from the group consisting of catecholamines, peptides, polypeptides, β1/β2-adrenoreceptor blocking agents, buplinarol, pindolol, alprenolol, cardiac glycosides, digitalis, palustrin, and ferulic acid; and a plurality of amino acids selected from the group consisting of alanine, arginine, aspartic acid, glutamic acid, histidine, isoleucine, leucine, methionine, phenylalanine, proline, serine, threonine, tryptophan, tyrosine, valine, and lysine that do not include asparagine, glutamine, and cysteine;
   a second chamber containing a second solution comprising one or more carbohydrates selected from the group consisting of monosaccharides, disaccharides, oligosaccharides, and polysaccharides; and
   a third chamber containing a priming solution comprising mannitol, sodium chloride, potassium chloride, magnesium sulfate heptahydrate, and sodium glycerophosphate.

2. The perfusion system of claim 1, wherein at least one of the first solution, second solution, or priming solution is sterilized prior to using the solutions to perfuse the heart.

3. The perfusion system of claim 1, wherein the one or more cardio stimulants includes epinephrine.

4. The perfusion system of claim 1, wherein the one or more carbohydrates in the second solution includes dextrose.

5. The perfusion system of claim 1, wherein the first solution includes adenosine.

6. The perfusion system of claim 1, wherein the first solution includes insulin.

7. The perfusion system of claim 1, wherein the first solution includes an immuno-suppressant.

8. The perfusion system of claim 1, wherein the first solution includes a multi-vitamin composition.

9. The perfusion system of claim 1, further comprising one or more electrolytes in the first solution.

10. The perfusion system of claim 9, wherein the one or more electrolytes includes calcium.

11. The perfusion system of claim 1, wherein the solutions are combined with a blood product prior to perfusing the heart.

12. The perfusion system of claim 1, further comprising a therapeutic agent.

13. A kit for use in a perfusion system that is configured for maintaining an ex-vivo heart in a functioning state under physiological or near physiological conditions, the kit comprising:
   a first solution comprising one or more carbohydrates selected from the group consisting of monosaccharides, disaccharides, oligosaccharides, and polysaccharides,
   a second solution comprising one or more cardio stimulants selected from the group consisting of catecholamines, peptides, polypeptides, δ1/β2-adrenoreceptor blocking agents, buplinarol, pindolol, alprenolol, cardiac glycosides, digitalis, palustrin, and ferulic acid; and a plurality of amino acids selected from the group consisting of alanine, arginine, aspartic acid, glutamic acid, histidine, isoleucine, leucine, methionine, phenylalanine, proline, serine, threonine, tryptophan, tyrosine, valine, and lysine that do not include asparagine, glutamine, and cysteine, and
   a priming solution comprising mannitol, sodium chloride, potassium chloride, magnesium sulfate heptahydrate, and sodium glycerophosphate,
   and a package.

* * * * *

UNITED STATES PATENT AND TRADEMARK OFFICE
CERTIFICATE OF CORRECTION

PATENT NO. : 10,039,276 B2
APPLICATION NO. : 14/734769
DATED : August 7, 2018
INVENTOR(S) : Waleed H. Hassanein et al.

It is certified that error appears in the above-identified patent and that said Letters Patent is hereby corrected as shown below:

In the Claims

Column 16, Line 25, Correct Claim 13 to read as follows:
13. A kit for use in a perfusion system that is configured for maintaining an ex-vivo heart in a functioning state under physiological or near physiological conditions, comprising:
    a first solution comprising one or more carbohydrates selected from the group consisting of monosaccharides, disaccharides, oligosaccharides, and polysaccharides,
    a second solution comprising one or more cardio stimulants selected from the group consisting of catecholamines, peptides, polypeptides, β1/β2-adrenoreceptor blocking agents, buplinarol, pindolol, alprenolol, cardiac glycosides, digitalis, palustrin, and ferulic acid, and a plurality of amino acids selected from the group consisting of alanine, arginine, aspartic acid, glutamic acid, histidine, isoleucine, leucine, methionine, phenylalanine, proline, serine, threonine, tryptophan, tyrosine, valine, and lysine that do not include asparagine, glutamine, or cysteine, and
    a priming solution comprising mannitol, sodium chloride, potassium chloride, magnesium sulfate heptahydrate, and sodium glycerophosphate,
    and a package.

Signed and Sealed this
Eighteenth Day of September, 2018

Andrei Iancu
*Director of the United States Patent and Trademark Office*